Figure 1:
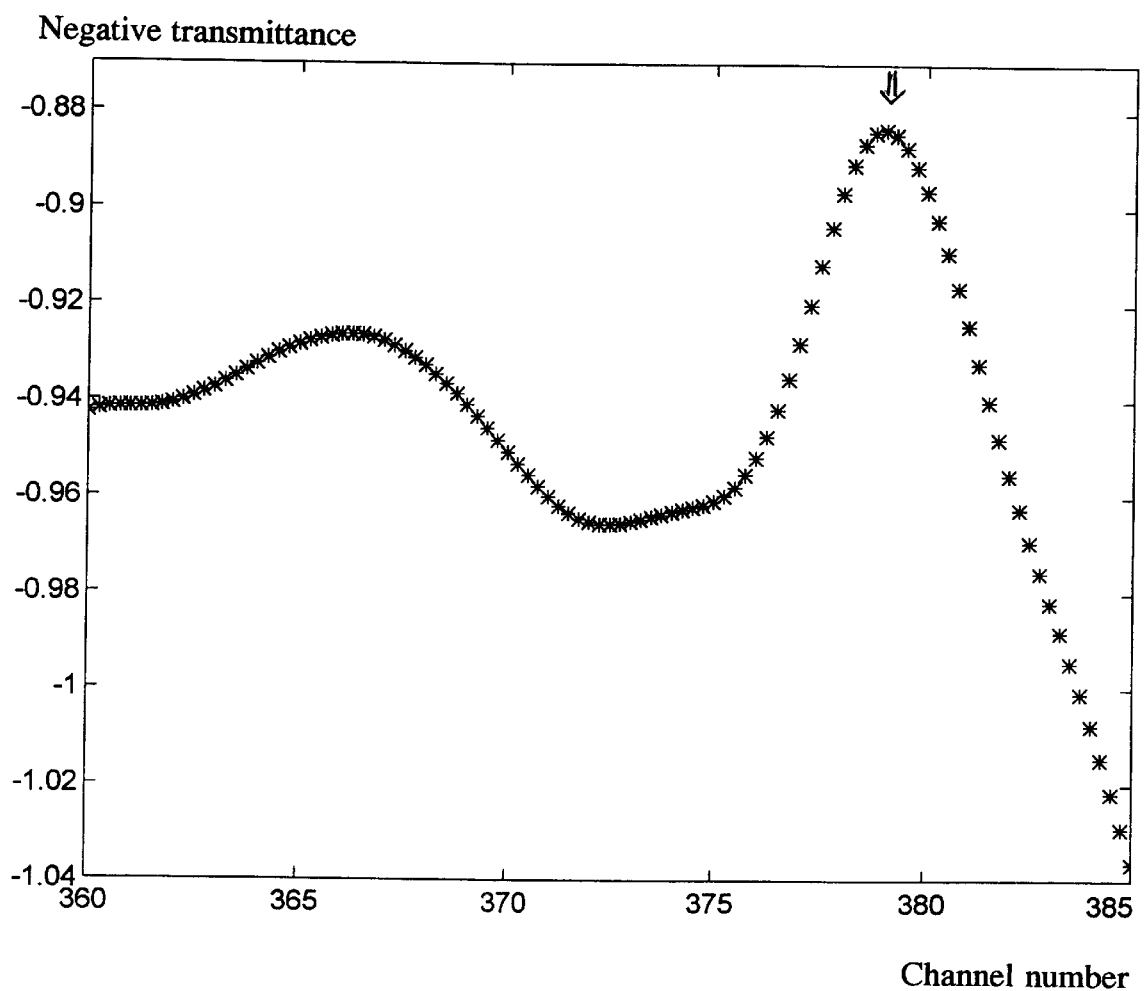

United States Patent [19]

Andersen et al.

[11] Patent Number: 5,933,792
[45] Date of Patent: *Aug. 3, 1999

[54] METHOD OF STANDARDIZING A SPECTROMETER

[75] Inventors: Hans Villemoes Andersen, Hilleroed; Lisa Kjaer, Hoersholm; Per Waaben Hansen, Hilleroed; Carsten Ridder, Broenshoej, all of Denmark

[73] Assignee: Foss Electric A/S, Hilleroed, Denmark

[*] Notice: This patent issued on a continued prosecution application filed under 37 CFR 1.53(d), and is subject to the twenty year patent term provisions of 35 U.S.C. 154(a)(2).

[21] Appl. No.: 08/624,470
[22] PCT Filed: Feb. 9, 1996
[86] PCT No.: PCT/DK96/00068
§ 371 Date: Apr. 3, 1996
§ 102(e) Date: Apr. 3, 1996
[87] PCT Pub. No.: WO96/24832
PCT Pub. Date: Aug. 15, 1996

[30] Foreign Application Priority Data

Feb. 9, 1995 [DK] Denmark ................... 0153/95
Jul. 21, 1995 [DK] Denmark ................... 0853/95

[51] Int. Cl.$^6$ ................................... G01N 21/27
[52] U.S. Cl. ................. 702/32; 702/85; 73/1.03; 356/303; 250/252.1
[58] Field of Search ................. 364/496, 497, 364/498, 499, 570, 571.01–571.08, 578; 356/303, 306, 317, 319, 326, 346, 243; 73/1.02, 1.03; 250/339.07–339.09, 341.5, 252.1; 702/32, 85

[56] References Cited

U.S. PATENT DOCUMENTS 5,121,337  6/1992  Brown ..................... 364/498
5,272,345  12/1993  Durham et al. .............. 250/373
5,545,895  8/1996  Wright et al. ............. 364/498 X
5,592,402  1/1997  Beebe et al. .............. 364/498

FOREIGN PATENT DOCUMENTS 0502495  9/1992  European Pat. Off. .
9007160  6/1990  WIPO .

*Primary Examiner*—Melanie A. Kemper

[57] ABSTRACT

A method for standardizing a spectrometer generating an optical spectrum from a sample, comprising generating at least one optical spectrum from at least one standardization sample each having a chemical composition resulting in the optical spectrum showing a characteristic pattern in a predetermined frequency range, comparing information relating to the pattern(s) to corresponding information relating to at least one reference pattern previously defined as the desired standard response from the at least one standardization sample, determining, based on the comparison, standardizing parameters describing the transition of the pattern (s) of the generated spectrum or spectra to the reference pattern(s) and storing said standardizing parameters in the spectrometer or a computer connected thereto, so that the spectrometer, when presented to an unknown sample, will, using the standardization parameters, generate an optical spectrum substantially identical to that which would be generated in a corresponding spectrometer standardized with a sample of the same chemical composition using the same previously defined reference pattern(s). The present method relates to standardization of the instrument to a well-defined state into which any number of instruments may be brought. In this state, calibrations may be transferred freely from instrument to instrument.

60 Claims, 9 Drawing Sheets

METHOD OF STANDARDIZING A SPECTROMETER

The present invention relates to the standardization of spectrometers generating an optical spectrum of a sample.

It has always been desired to be able to manufacture spectrometers which generate the same spectra when exposed to the same sample. However, due to the extreme sensitivity of spectrometers to the optical properties of the samples and, to the other optical elements of the spectrometers, this has proven impossible.

The optimal instrument would be an instrument of which identical copies could be manufactured and the measurements of which, in addition, never drifts. This means that the same calibration may be used throughout the life time of the instrument and, which is equally important, that calibrations may be developed on any instrument and may be freely transferable to all other instruments. The best alternative to this instrument would be a method of standardizing all instruments into a well defined state in which the above interchangeability of calibrations was possible.

As it will be impossible to manufacture identical spectrometers, work has been done in the field of attempting to standardize the instruments and, therefore, decrease the work load required by subsequent spectrometers, once a first spectrometer has been fully calibrated.

Ruhl (WO 93/03341) has worked with the concept of determining the spectrum of an etalon as well as the development of a calibration on a master instrument and subsequently transferring the etalon and the calibration to a field instrument which will seemingly require no further calibration. In this reference, the spectrum of the sample alone and the sample together with the etalon are subtracted in order to generate the spectrum of the etalon alone. On the basis of this etalon spectrum and a reference spectrum of the etalon, the spectrum of the sample is corrected accordingly.

However, the method of Ruhl generates a number of strictly individual references (etalons) which all have to be introduced into the master instrument. In order to generate additional slave instruments, the master instrument must exist and should, which is not possible, be exactly the same each time additional etalons are introduced and each time a new calibration is developed. If the master instrument is not exactly the same each time, the old calibration will not suit the new slave instruments or the new calibration will not suit the old slave instruments. The only solution is a re-measurement of all etalons in all slaves. Thus, the method of Ruhl does not solve the above task completely, as the method of this reference does not provide complete interchangeability of calibrations and more or less complete standardization of the instruments.

The method of Ruhl, due to the position of introduction of the etalon, corresponds to performing a determination of the background spectrum. This means that this method does not take into account the difference in light absorption when e.g. a sample holding cuvette is replaced. This is preferably avoided, as this will typically influence the operation of the spectrometer.

Also others have worked in the field of changing the state of an instrument in order to avoid a demanding re-calibration of the instrument: Yongdong Wang et al.: "Improvement of Multivariate Calibration through Instrument Standardization", Anal. Chem. 1992, 64, pp 562–64, Shenk et al. U.S. Pat. No. 4,866,644, Pittaro et al. U.S. Pat. No. 5,341,206, Maggard U.S. Pat. No. 5,243,546 and Ganz EP-A-0 560 006.

These methods either describe how to transform an instrument from its present state to its initial state or how to transform the present state of one instrument to the present state of another instrument. However, none of these methods describe how to transform an instrument to a well defined state—and preferable a state into which any number of instruments may be transformed.

However, a method of the above type is, in fact, provided by the present invention of which a first aspect relates to a method for standardizing a spectrometer generating an optical spectrum from a sample, comprising generating at least one optical spectrum from at least one standardization sample each having a chemical composition resulting in the optical spectrum showing a characteristic pattern in a predetermined frequency range, comparing information relating to the pattern(s) to corresponding information relating to at least one reference pattern previously defined as the desired standard response from the at least one standardization sample, determining, based on the comparison, standardizing parameters describing the transition of the pattern(s) of the generated spectrum or spectra to the reference pattern(s) and storing said standardizing parameters in the spectrometer or a computer connected thereto, so that the spectrometer, when presented to an unknown sample, will, using the standardization parameters, generate an optical spectrum substantially identical to that which would be generated in a corresponding spectrometer standardized with a sample of the same chemical composition using the same previously defined reference pattern(s).

In the present context, a "transition" of a pattern "to" another pattern is a transition of the pattern into a pattern which only differs from the other pattern by a trivial difference, such as a constant offset or a constant factor. Total identity is not required but is, naturally, presently preferred.

In addition, using the hard modelling of this preferred embodiment, much less information may be required in order to perform the standardization. Therefore, only the information present in a number of predetermined frequency ranges need be used. Presently, these frequency ranges may have a width in frequency wide enough for being able to contain e.g. one or more absorption peaks of the spectrum. On the other hand, they may be very narrow (such as a single "pin" in a FTIR spectrometer) so as to only contain e.g. the peak of an absorption peak in the spectrum, depending on characteristics of the model used (on the amount of information required thereby).

A "characteristic pattern" is, in the present context, a pattern which may be determined or identified in a repeatable manner by an automated process. Patterns that do not have this ability are not preferred in the present method, as these may not lead to repeatable results.

According to this first aspect of the invention, standardized spectrometers will generate substantially the same spectra when exposed to the same sample, so that the method of the invention actually transforms the spectrometers to a well defined state from which calibrations and data may be freely transferred from one standardized spectrometer to another standardized spectrometer.

Thus, according to the present invention, one or more standardization samples is/are introduced into the spectrometer and the optical spectra thereof are generated. Information relating to one or more characteristic patterns of these one or more spectra is/are compared to corresponding information from reference patterns which are defined as the desired standard responses of the instrument. Thus, prior to the standardization, a standard response has been defined, and the standardization operates to transfer the state of the spectrometer in order to obtain this standard response. This standard response characterises the state into which the spectrometer is transferred during the standardization.

Thus, the reference pattern(s) define a state or desired standard response of the spectrometer in the predetermined frequency ranges when measuring on the standardization sample(s) As these reference pattern(s) do not relate directly to another instrument, the reference or standard state into which the standardized instrument is put during standardization is independent of any current state of an instrument and is solely determined on the predefined reference pattern (s). This, naturally, means that the standard state may be obtained at any time as long as the standardization sample(s) and reference pattern(s) is/are available.

This is a major difference from the majority of the prior methods which require the existence of a reference instrument. As this instrument will drift as all other instruments, the reference state will drift. That problem is not encountered in the present invention.

The actual transformation required in order to transform the spectrometer will depend on how the spectrometer differs from the standard state, that is, what effects should be counteracted.

In general, two types of methods may be used for standardizing instruments of the present type: hard modelling and soft modelling. The soft modelling is a modelling wherein the transformation or shift of the individual parts of the response (spectrum) is calculated and stored without any assumptions being made as to the nature or mathematical type of the translation or shift required or the physical changes causing it.

In the extreme case, the predefined frequency range and the characteristic pattern may have a frequency range identical to or at least as wide as the frequency range of the full spectrum obtained of the samples.

Hard modelling, on the other hand, is a modelling where assumptions are made as to the nature or the mathematical identity or type of the shift or translation required. This reduces the complexity of the calculation and the number of variables required in order to describe the required translation. Using hard modelling, translation required of one part of the spectrum may be predicted based on the translation of another part of the spectrum. Therefore, the required translation of a spectrum only has to be known for parts of the spectrum in order for it to be determined or predicted for the remaining part of the desired spectrum.

In a preferred embodiment, the present method for standardizing a spectrometer generating an optical spectrum from a sample, is a method wherein the optical spectrum comprises a frequency range wherein the spectrometer is to be standardized, and which method comprises:

generating at least one optical spectrum from at least one standardization sample each having a chemical composition resulting in the optical spectrum showing characteristic patterns in one or more predetermined frequency ranges, the one or more frequency ranges covering only a part of the frequency range to be standardized, comparing information relating to the characteristic pattern(s) to corresponding information relating to reference pattern(s) previously defined as the desired standard response(s) for the at least one sample, determining, based on the comparison of the information and a model predicting, on the basis of deviations between information in the individual pattern(s) of the generated spectrum or spectra from that of the corresponding reference pattern(s), transformation of parts of the frequency range to be standardized not being in the one or more predetermined frequency ranges, standardizing parameters defining transition of the pattern(s) of the generated spectrum or spectra to the reference pattern(s) and of the remainder of the frequency range to be standardized, storing said standardizing parameters in the spectrometer or a computer connected thereto, and in the spectrometer using the stored standardizing parameters for generating, when presented to an unknown sample, an optical spectrum substantially identical to that which would be generated in a corresponding spectrometer standardized with at least one standardization sample of the same chemical composition(s) using the same previously defined reference pattern (s).

Using hard modelling, depending on the complexity of the assumed mathematical description of the translation, only the translation of a relatively few and small parts of the spectrum need be known or determined.

In typical spectrometers for generating optical spectra from samples, a light emitter and a light detector are comprised which define a light path into which the sample in question is positioned in order to have the sample interact with the light. Typically, the spectrometer additionally comprises means for holding the sample, such as a sample cuvette for holding liquid samples, the material of which additionally interacts with the light. Furthermore, mirrors, prisms, gratings, lenses and the like may also be introduced in the light path in order to influence the light.

All the above optical elements may vary over time: the intensity and wavelength-dependence of the light emitter may vary, the sensitivity of the light detector, the thickness of a sample cuvette and the position of the optical elements may all vary. All these variations will influence the output of the light detector and, thus, the spectrum generated by the spectrometer.

Typically, the drift of the spectrometer may be described as a frequency drift as a cause of which the same wavelength may not be represented identically by two otherwise similar spectrometers, and an intensity drift in which different intensities are measured at the same wavelengths for the same sample in two otherwise similar instruments.

In order to take into account the potential drift of all optical elements in the spectrometer, it is preferred that the standardization sample or samples is/are introduced and handled in the spectrometer in the same manner as unknown samples to be measured. In this manner, no additional optical elements need be introduced in the light path the effect of which may introduce an additional effect, which may be compensated for, but which is not present when performing measurements on normal samples.

In the present context, it is preferred that the spectrometer generates a continuous spectrum of the sample. This type of spectrometer may employ a stationary or movable grating and stationary or movable detector or detectors or any other suitable means. The presently preferred spectrometer is, however, one which employs Fourier transformation.

Spectrometers generating a continuous spectrum have a number of advantages over spectrometers which generate information relating to discrete wavebands. The operator has access to the continuous spectrum without having to remove or replace optical elements present in the light path of the spectrometer. This removal or replacement may introduce additional errors in the spectrometer.

The optical spectrum of this type of spectrometer is typically an electromagnetic spectrum in a given frequency range, preferably an absorption spectrum, a transmission spectrum or a reflection spectrum. However, also emission spectra, such as fluorescence spectra or Raman spectra, may equally well be used in connection with the present method.

Naturally, optical spectra may be generated from virtually any type of sample, such as gaseous samples, solid samples, such as cheese, grain or meat, or liquid samples, such as milk or milk products. In general, optical spectra are often used in order to characterize, that is, determine the concentration of chemical components therein, a wide variety of products, such as dairy products.

It is presently preferred that the spectrometer is a spectrometer adapted to handle liquid samples, and that the standardization sample is a liquid sample. In this situation, the standardization sample may be introduced into the spectrometer in a sample cuvette, if present, in the same manner as a normal sample. Thus, no additional elements need be introduced in the spectrometer during standardization, whereby the standardization will not have to take into account elements which will not be present under a measurement of a normal sample.

Depending on the type of standardization required in the individual situations, the characteristic pattern may be required to comprise more or less information from the optical spectrum of the standardization sample in order to facilitate the standardization.

A characteristic pattern may be as little as a local maximum or minimum or an inflexion of the spectrum. On the other hand, it may be a larger part of the spectrum, all depending on the amount of information required in order to perform the actual standardization.

At present, it is preferred that a characteristic pattern comprises one or more local maxima or minima of the optical spectrum or in one of its derivatives.

When standardizing the frequency axis of a spectrometer, it will be required to obtain information relating to one or more well defined frequencies in the characterizing pattern (s). Thus, it is preferred that the characteristic pattern(s) comprise one or more local maxima or minima in the optical spectrum positioned at fixed frequencies on the frequency axis of the spectrum. Preferably, the fixed frequencies are frequencies characteristic to the identity of one or more chemical constituents of the standardization sample.

In this manner, the frequency position of the local maxima or minima will be well defined, as they are defined by nature. In addition, it is preferred that the chemical composition of the standardization sample is one which is within such concentration tolerances that the fixed frequencies are unambiguously identified by the local maxima or minima, as other components in the sample may "hide", "overwrite" or shift the local maximum or minimum in question if present in a too high concentration.

The method of the invention is not limited to any specific type of spectrometer or any specific type of sample. The standardization of the instrument is solely performed on the basis of the introduced standardization sample(s) and the corresponding reference pattern(s). Thus, as soon as the reference pattern(s) and the chemical composition of the standardization sample(s) are defined, any number of spectrometers may be standardized, and a spectrometer may be standardized any number of times.

This concept has to the knowledge of the applicant not been seen before. In addition, this concept is the optimal standardization, as this standardization has virtually no boundaries as long as the standardization sample may be reproduced and as long as the reference pattern may be safely stored and introduced or re-introduced into spectrometers when required.

As a practical feature, it is naturally preferred that the standardization sample(s) is/are stable over a given amount of time, as it will be preferred to manufacture these at a single plant and therefrom transfer it to the other parts of the world.

Thus, the standardization sample(s) is/are preferably stable to such an extent that they will fulfil the above-mentioned condition after storage at 20° C. in a sealed container for at least 1 year, preferably 2 years, after the production and packing of the sample.

Another practical point in the selection of one or more suitable standardization sample(s) is that the contents thereof should be as harmless as possible to an operator of the spectrometer. At present, it is preferred that the components of the standardization sample(s) the identity of which is decisive to the frequencies of the local maxima or minima are selected from mixtures of water and lower alcohols, such as where the components are constituted by a mixture of water and propanol.

Depending on the amount of information required in order to obtain standardization according to the invention, one or more standardization samples may be desired or required. If information is desired in a number of wavebands or predetermined frequency ranges, a single standardization sample may be produced having all the desired characteristic patterns in its optical spectrum or a number of standardization samples may be produced so that these together provide the information desired.

At present, a hard model is preferred requiring only information in two predetermined frequency ranges. This information may be provided by using only a single standardization sample. Reducing the number of standardization samples required at the same time reduces the probability of failure in the standardization method due to the operator e.g. interchanging the samples and thereby misleads the calculations.

This mixture may be a mixture of water and propanol having a concentration of propanol in the range of 1–5% w/w, the concentration being within a tolerance of ±10% relative, preferably less than ±5wt. % relative, such as less than ±2 wt. % relative, preferably less than −1 wt. % relative, such as less than ±0.5 wt. % relative, preferably less than ±0.25 wt. % relative.

At present, the preferred standardization liquid for use in the single, preferred standardization sample, comprises water and propanol having a concentration of 3.83 w/w% of propanol. However, as it is preferred to have a standardization liquid which has a long shelf life, it may be preferred to add one or more preservatives, such as bronopol, potassium dichromate, sodium azide, azidiol, benzalkonium chloride, sodium benzoate, cathone, sodium sulphite, nisin, sorbic acid, thiabendazole, biphenyl, benomyle, methylparaben or ethylparaben.

In addition, it may be preferred to add a pH buffer to the liquid in order to have a constant pH in the sample. A changed pH may change the absorbance in certain wavebands of the liquid. Possible pH buffers may be: citrate, phosphate, acetate, borate and TRIS.

The desired concentration of the preservatives in the presently preferred standardization liquid will depend on, on the one hand, the desired shelf life of the liquid and, on the other hand, the influence of the preservatives on the position and size of the absorption peaks in the liquid. It is presently contemplated that concentrations in the interval 0.02–0.10 w/w% may be desired. However, depending on the optical spectrum of the actual preservative, a larger or smaller concentration may be required in order to ensure that the positions and the sizes of the absorption peaks are not altered to any excessive degree.

Yet a practical note will be that it is presently preferred to use the preferred standardization liquid as soon as possible after opening of the container as the propanol therein will evaporate after a very short time. In order to reduce this evaporation, it is furthermore recommended that the liquid be refrigerated before use.

As not only the frequency axis but also the absorbance axis of the spectra generated by the spectrometer is preferably standardized, it will typically be required not only to have information from the standardization liquid(s) relating to well defined frequencies but also to well defined absorbances. Thus, it is preferred that the concentration(s) of the components of the standardization sample(s) is/are kept within such tolerances that any error on the amplitude axis of the spectrum ascribable to concentration variations in the standardization sample is less than the repeatability of the spectrometer. In this situation, also information relating to well defined absorbances may be obtained from the spectrum or spectra of the standardization liquid(s) for use in the standardization of the spectrometer.

When performing the standardization of the frequency axis of spectra generated by the spectrometer, the comparison of the information relating to the measured pattern(s) to corresponding information relating to the reference pattern (s) preferably comprises identifying the frequencies in the measured pattern(s) at which local maxima or minima corresponding to local maxima or minima in the reference pattern(s) are positioned. In this situation, the determination of standardizing parameters suitably comprises determining the relation between the identified frequencies in the measured pattern(s) and the corresponding frequencies in the reference pattern(s), whereby parameters describing the frequency relation may be obtained.

These parameters may subsequently be used for correcting the frequency axis of spectra generated from unknown samples in order to standardize this axis of this new spectrum.

For use in the standardization of the amplitude or absorbance axis of the spectrometer, it may be preferred that the determination of standardizing parameters comprises determining the relation between the amplitudes of the measured pattern(s) at the identified frequencies and the amplitudes of the reference pattern(s) at the corresponding frequencies, and obtaining parameters describing the relation. This is the simplest method, as these peaks are well defined and are already identified in the course of the frequency-correction.

The actual relation between the amplitude of the characterizing pattern(s) of the standardization liquid and the corresponding amplitude of the reference pattern(s) will depend heavily on the actual drift of the spectrometer which is to be counter-acted. However, in the presently preferred spectrometer type, the FTIR instrument, hard modelling may be used assuming the relation to be a linear function of the absorbance (see Example 1).

When performing the standardization of the frequency axis of the generated at least one spectrum, the generated optical at least one spectrum is/are suitably transformed using the parameters describing the frequency relation between the local maxima or minima so as to obtain at least one transformed spectrum in which at least the identified local maxima or minima are positioned at substantially the same positions as in the reference pattern(s). This has the advantage that, subsequently to this transformation, corresponding frequencies of the reference pattern(s) and of the transformed at least one spectrum and the amplitudes measured therein may be determined.

This facilitates the preferred comparison, over at least one frequency range, of the amplitude of the at least one frequency-transformed spectrum and the corresponding amplitude of the reference pattern(s), whereby standardization parameters describing the relation between the amplitude of the at least one frequency-transformed spectrum and the amplitude of the reference pattern(s) may be obtained.

Thus, on the basis of the above standardization, standardization parameters will be obtained which may be used for standardizing a spectrometer in accordance with the reference pattern(s).

In fact, even though it is presently preferred to base the standardization of the spectrometer on an absorption spectrum of the reference sample, the present invention is not limited thereto. In the situation where the spectrometer is an FTIR instrument, the absorption spectrum, the so-called single beam spectrum which is the spectrum not corrected for the background (typically solvents such as air, alcohols or water) and even the interferogram from which the single beam spectrum is derived may all form the basis of the standardization. This is due to the fact that, knowing the background, any of these spectra may be found from any other of the spectra.

Thus, especially in FTIR instruments, the present standardization may also be performed on the basis of e.g. single beam spectra, intensity or transmittance spectra, interferograms, etc.

According to the present invention, the reference pattern (s) may be derived from a spectrum or spectra generated by a spectrometer on the basis of at least one sample of substantially the same chemical composition(s) as the at least one standardization sample(s) or may be determined or defined in any other suitable manner depending on the actual type of standardization samples used. For example, if only a standardization of the frequency axis is desired, the frequencies of absorption peaks of standardization samples may be derived from tables and used as reference patterns or reference information instead of deriving this information from ones own measurements on the samples.

Preferably, the characteristic pattern(s) of the optical spectrum of the at least one standardization sample is/are known or optionally pre-defined at the time of generating the optical spectrum from the at least one standardization sample. In this manner, the mathematical nature of the translation may be known or assumed on beforehand.

Depending on the actual type of spectrometer and of variation to be taken into account using the present standardization, the mathematical model of the hard modelling, if used, will vary.

Preferably, the model assumes an interrelation between the positions on the frequency axis of at least parts of the characteristic patterns of the optical spectrum of the at least one standardization sample and the corresponding parts of the reference patterns. This assumed interrelation may be a linear interrelation.

The model may optionally or additionally assume an interrelation between the positions on the absorption axis of at least parts of the characteristic patterns of the optical spectrum of the at least one standardization sample and the corresponding parts of the reference patterns. This assumed interrelation may be a linear interrelation or a first-order interrelation.

One of the advantages of the present invention, and especially if used in connection with a hard modelling, is that the at least one standardization sample may be of a type which is different in chemical composition from the unknown sample. Thus, using the present invention, the standardization is not limited to a type of sample which may be hostile or volatile, which may have an unsuitably short shelf life or which are difficult or impossible to reproduce. It will be possible to define and produce standardization samples having along shelf life and which are easily reproduced.

In addition, depending on the translations required and the complexity and requirements of any mathematical model predicting those, preferably 1–100, such as 1–80, preferably 1–10, such as 2–5, preferably 2 characteristic patterns and/or reference patterns are used.

In fact, especially when hard modelling is used (the preferred embodiment of aspect one) it may be preferred that the total coverage of the one or more predetermined frequency ranges cover not more than 90%, such as not more than 70%, preferably not more than 50%, such as not more than 30%, preferably not more than 20%, such as not more than 10%, preferably not more than 5% of the frequency range to be standardized.

In a second aspect, the present invention relates to a method for obtaining a standardized optical spectrum of an unknown sample, the method comprising measuring an optical spectrum of the unknown sample using a spectrometer which has been standardized according to the above method and transforming the measured spectrum into a standardized spectrum by applying the standardization parameters obtained from the standardization of the spectrometer and stored in the spectrometer or a computer connected thereto.

Thus, according to this second aspect, a spectrometer may be standardized to the same, predefined state at any time. This is typically required at least once a month due to the normal unavoidable drift of spectrometers, but additionally when optical elements of the spectrometer have been replaced or altered.

In a third aspect, the present invention relates to a method for standardizing a plurality of spectrometers each of which generates an optical spectrum from a sample, the method comprising:

generating, in each spectrometer, at least one spectrum from at least one standardization sample each having a chemical composition resulting in an optical spectrum showing a characteristic pattern in a predetermined frequency range, comparing, in each spectrometer, information relating to the pattern to corresponding information relating to a reference pattern previously defined as the desired standard response for the at least one standardization sample, determining, in each spectrometer, based on the comparison, standardizing parameters defining transition of the pattern of the generated spectrum to the reference pattern, and storing, in each spectrometer or one or more computers connected thereto, said standardizing parameters, the respective standardization samples having substantially identical chemical compositions so that they correspond to the same respective desired standard response, so that each of the standardized spectrometers, when presented to the same unknown sample, using the stored standardization parameters, will generate substantially identical optical spectra.

As mentioned in relation to the first aspect of the invention, in a preferred embodiment, assumptions are made as to the nature and the mathematical type of translation required, in order to be able to use a hard modelling.

Thus, a preferred embodiment of this third aspect of the present invention relates to a method for standardizing a plurality of spectrometers each of which generates an optical spectrum from a sample, wherein at the optical spectra comprise a frequency range wherein the spectrometers are to be standardized, the method comprising:

generating, in each spectrometer, at least one spectrum from at least one standardization sample each having a chemical composition resulting in an optical spectrum showing characteristic patterns in one or more predetermined frequency ranges, the one or more frequency ranges covering only part of the frequency range to be standardized, comparing, in each spectrometer, information relating to the pattern(s) to corresponding information relating to reference pattern(s) previously defined as the desired standard response for the at least one standardization sample, determining, in each spectrometer, based on the comparison of the information and a model predicting, on the basis of deviations between information in the individual pattern(s) of the generated spectrum or spectra from that of the corresponding reference pattern(s), transformation of parts of the frequency range to be standardized not being in the one or more predetermined frequency ranges, standardizing parameters defining transformation of the pattern(s) of the generated spectrum or spectra so as to correspond to the reference pattern(s) and of the remainder of the frequency range to be standardized, storing, in each spectrometer or one or more computers connected thereto, said standardizing parameters, the respective standardization samples having substantially identical chemical compositions so that they correspond to the same respective desired standard response, so that each of the standardized spectrometers, when presented to the same unknown sample, using the stored standardization parameters, will generate substantially identical optical spectra.

In this context, that the standardization samples have "substantially identical compositions" means that they should produce optical spectra having substantially identical characteristic patterns. No demands are put to the standardization sample(s) as to the optical spectra between or outside the predetermined frequency ranges.

This illustrates the strength and applicability of the present invention, as any number of spectrometers may be transferred into substantially the same state, where substantially the same spectrum of an unknown sample will be generated on all the standardized spectrometers. This has a number of utilities, one of the most obvious being the free transferability of calibrations. This will be described below.

Thus, in a fourth aspect, the present invention relates to a method for calibrating a spectrometer which generates an optical spectrum from a sample, comprising standardizing the spectrometer as described above and introducing into the spectrometer calibration coefficients, typically from a multivariate calibration, established on the basis of measurements performed on one or more other spectrometers which have been subjected to the same standardization.

According to the general nature of the invention, the calibration coefficients may be established on the basis of measurements performed on any number of spectrometers, as long as these spectrometers have been subjected to the same standardization and, if reliable results are desired, as long as the chemical reference method used for the determination of the concentrations of the components is the same.

A typical use of a calibration is a calibration performed with respect to the prediction of the concentration of one or more components in a sample.

A calibration typically enables an instrument to predict the concentration of a component by multiplying the absorbance at a certain wavelength or in a certain waveband of the spectrum by a given factor and additionally or optionally multiply other absorbances with other factors in order to take into account the effects of other components.

As the absorbance measured at a certain wavelength will depend not only on the absorption of the sample but also on the intensity emitted by the light emitter, the thickness of the sample cuvette and the sample cuvette material, the reflection of any mirrors in the optical path, the sensitivity of the detector a.s.o., this absorbance depends also on the actual instrument used for the measurement of the absorbance. This is the main reason that calibrations, until now, have not been freely transferable between instruments.

Using the standardization according to the invention, however, the above effects will not be removed but will be compensated for, whereby a calibration developed on one or more standardized instrument(s) may now be used on another, as these effects are taken into account in the calibration of the instrument on which this has or have been developed has been standardized.

The interchangeability of calibrations will be described in Example 2.

Figure 2:
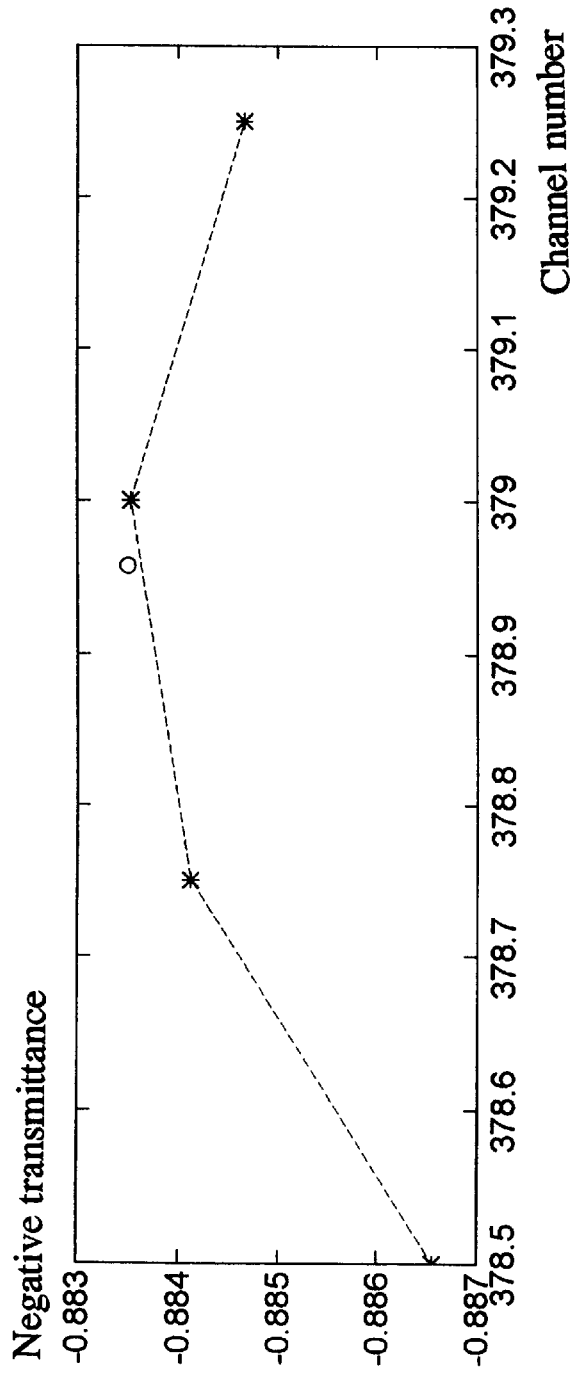
Figure 3:
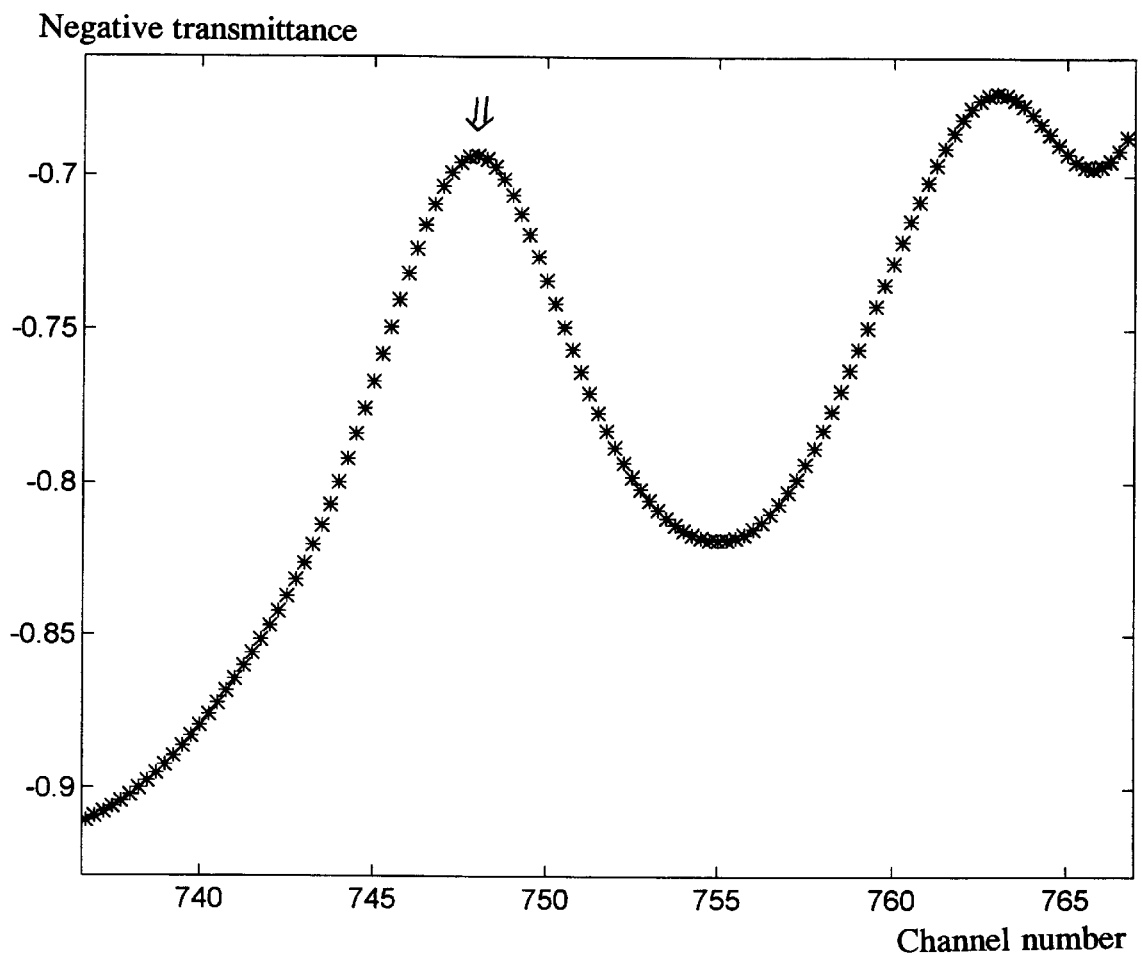
Figure 4:
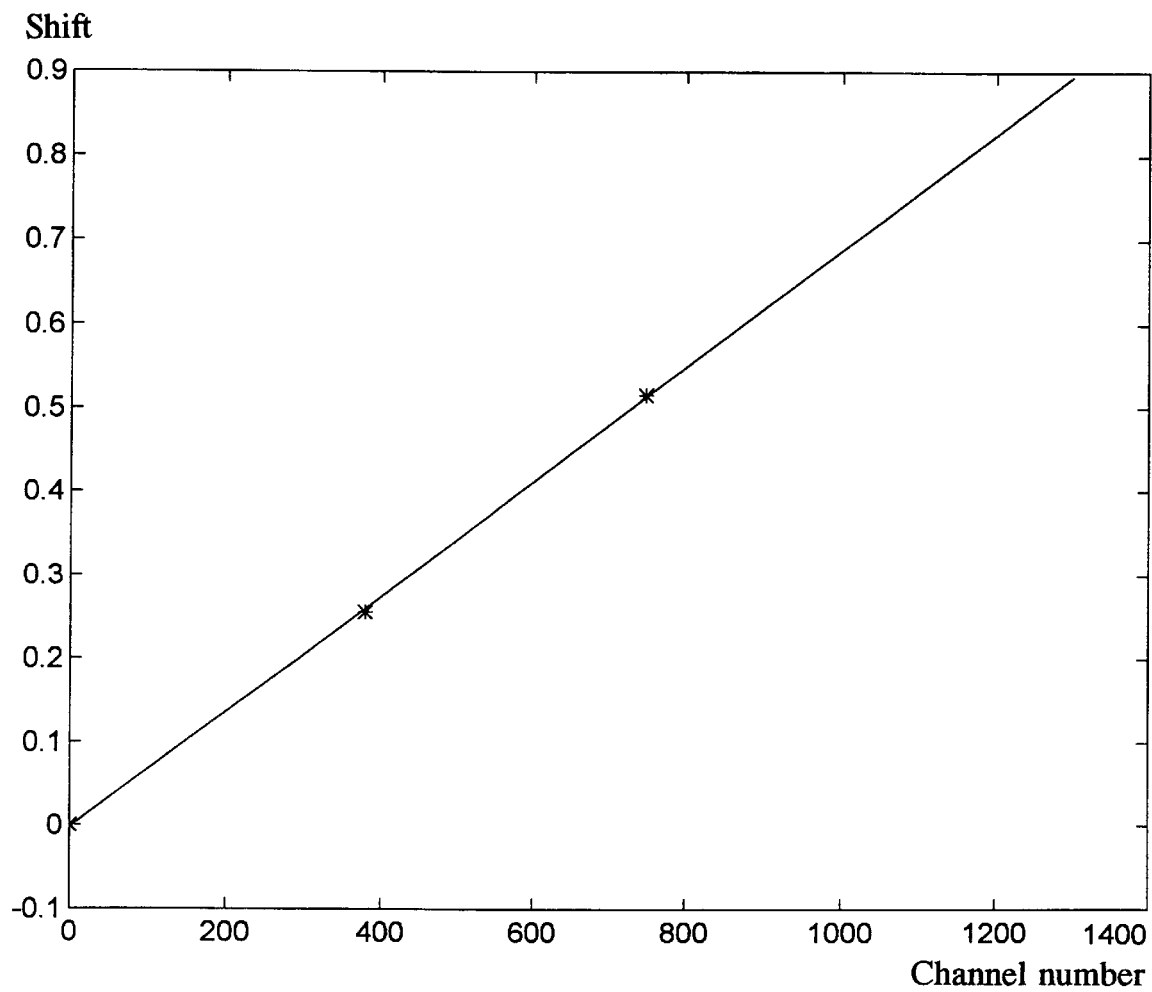
Figure 5:
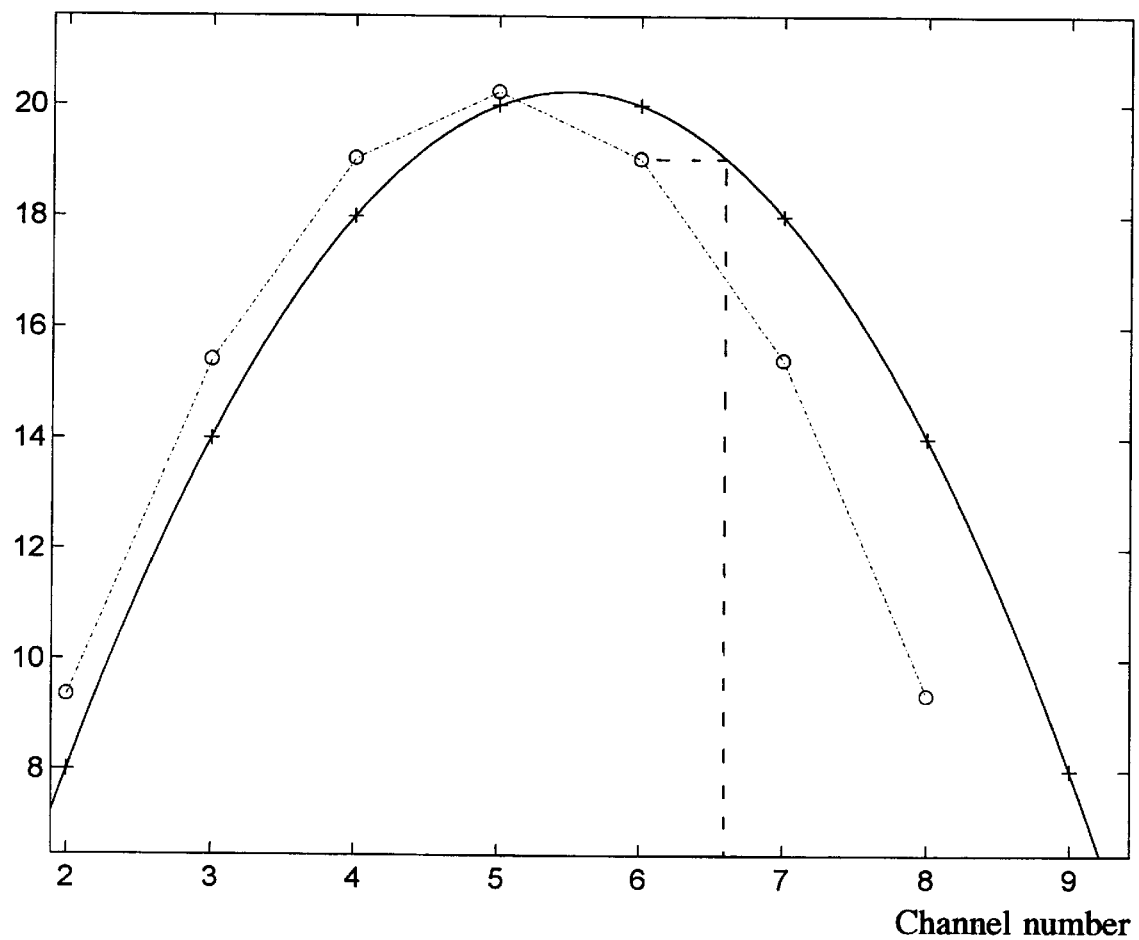
Figure 6:
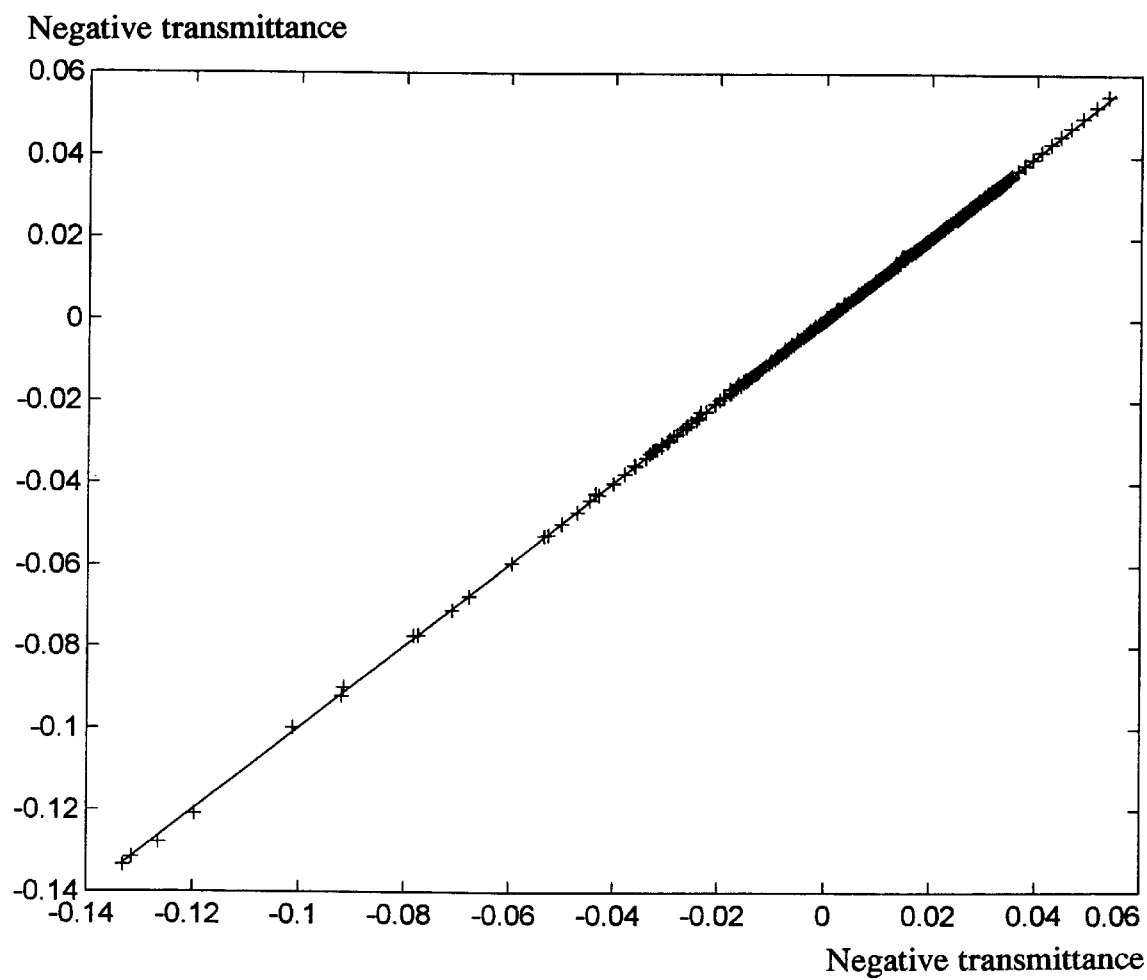
Figure 7:
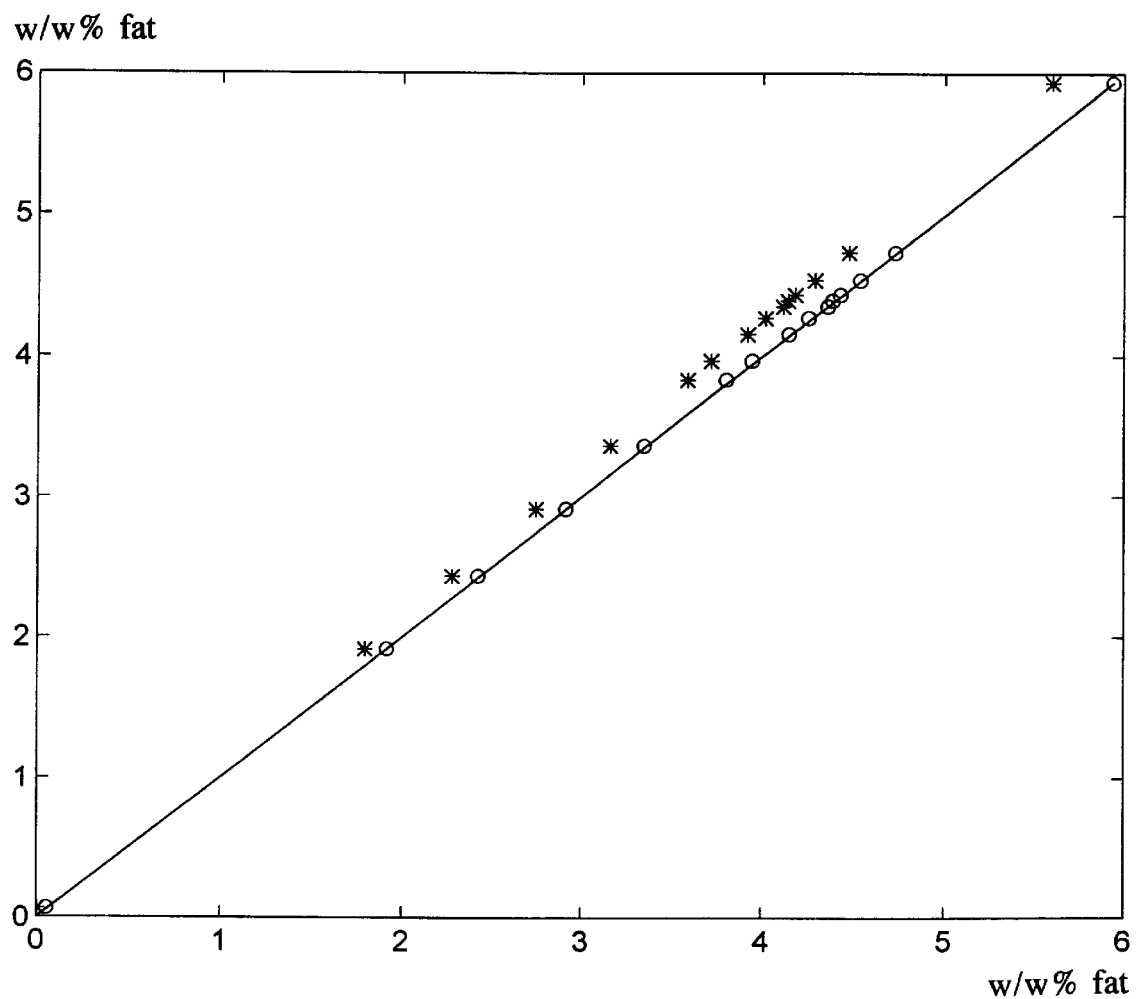
Figure 8:
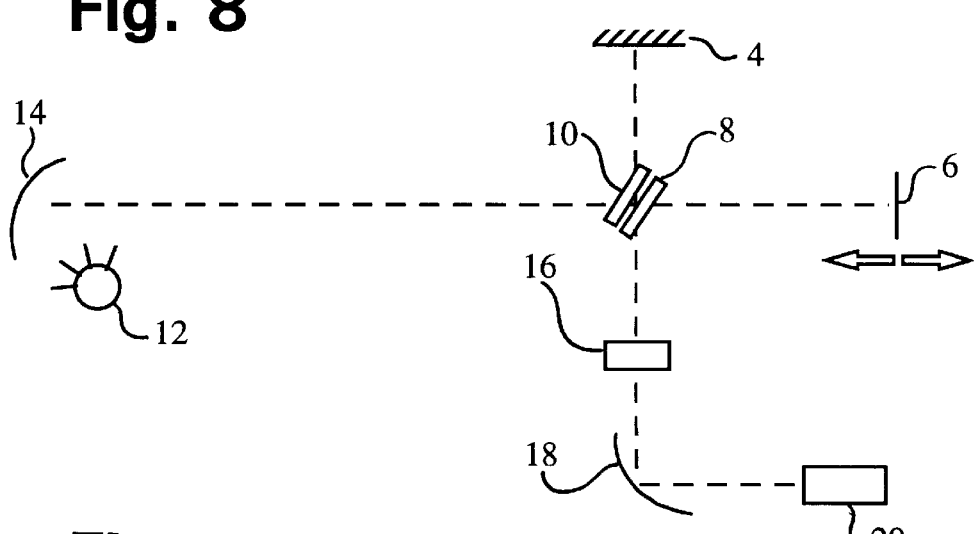
Figure 9:
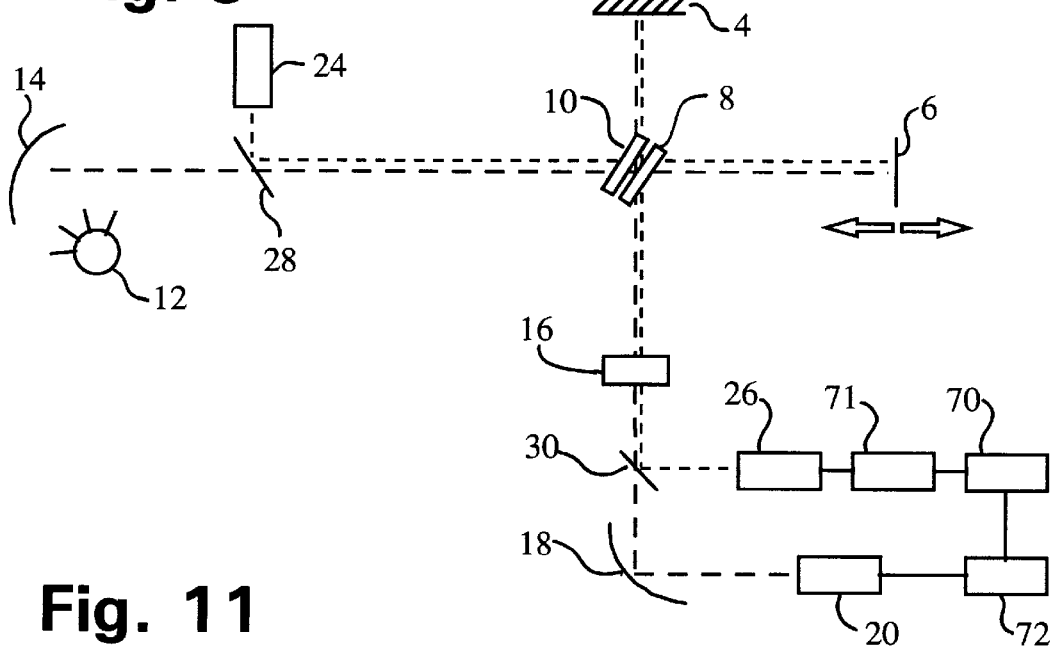
Figure 11:
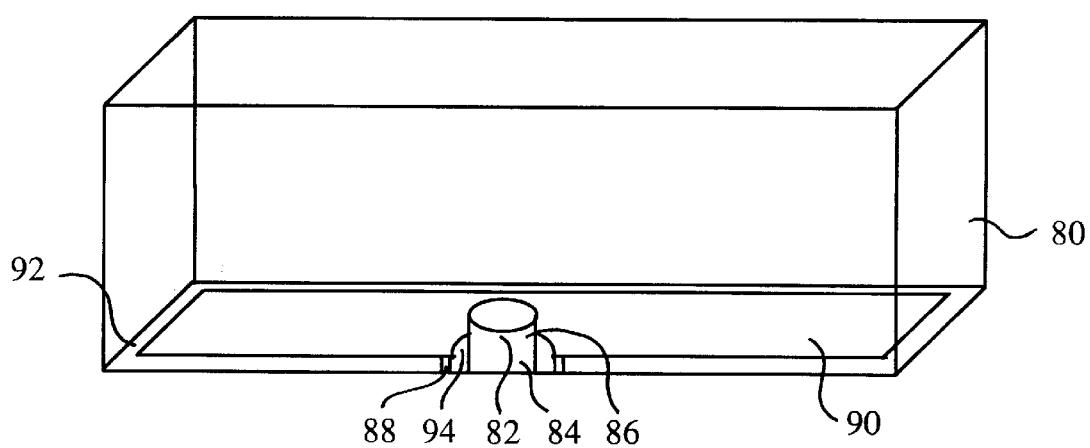
Figure 10:
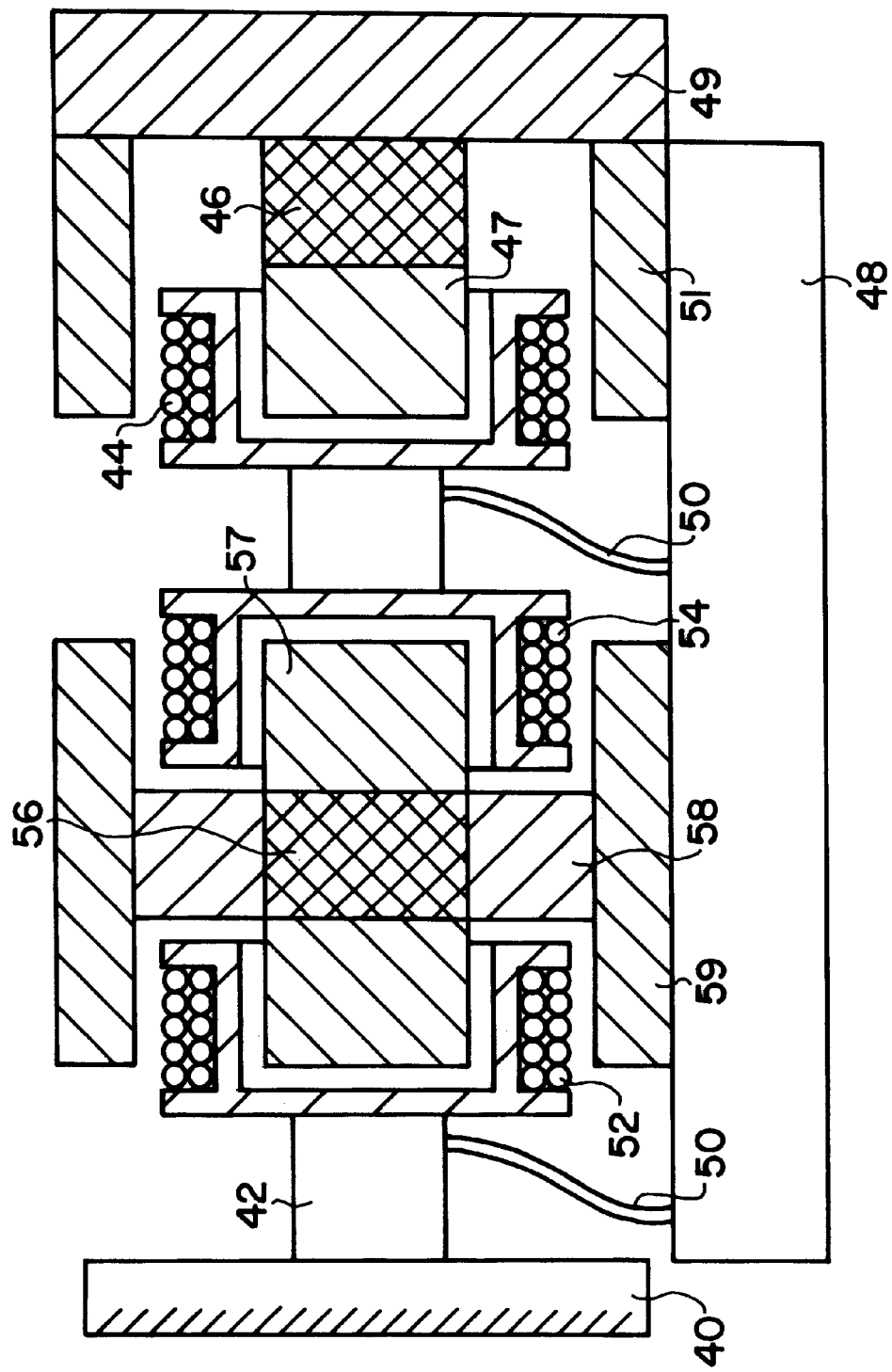

A presently preferred embodiment of the standardization of the present invention will be described below in two examples and with reference to the drawing on which:

FIG. 1 illustrates the negative transmission spectrum of a reference sample in the vicinity of a first absorption peak, FIG. 2 illustrates the four points closest to the peak position of the first peak and the determined peak position, FIG. 3 illustrates the negative transmission spectrum of a reference sample in the vicinity of a second absorption peak, FIG. 4 illustrates the linearity of the frequency correction, FIG. 5 illustrates the frequency correction of a spectrum, FIG. 6 illustrates the linearity of the absorbance correction, FIG. 7 illustrates the improvement in the predicted values of a standardized instrument compared to an instrument not standardized, FIG. 8 is an illustration of a typical interferometer, FIG. 9 illustrates the interferometer of FIG. 8 further using a Phase Locked Loop, FIG. 10 illustrates the preferred driver for the movable mirror of the preferred interferometer, and FIG. 11 illustrates the preferred surroundings for the interferometer.

EXAMPLE 1

Standardization of an FTIR instrument

In the present example, a standardization of a typical FTIR instrument will be described. The present instrument is equipped for performing measurements on liquids and is, thus, equipped with a sample cuvette for holding the sample during the measurement.

In the present example, the spectrum obtained from the sample is a transmission spectrum obtained by transmitting infra red light from the interferometer through the sample cuvette and onto a detector.

In this type of instrument, the typical manner of obtaining the transmittance spectrum of a sample is first to obtain a so-called single beam spectrum which comprises information relating to both the transmission of the sample, sample cuvette a.s.o., the reflection of mirrors, emission spectrum of the light emitter and the sensitivity of the detector and other effects. In order to isolate the transmission of the sample, a similar spectrum is then measured on a so-called zero-liquid wherein the same effects are comprised, but wherein the sample is not present. These two spectra are subsequently divided in order to obtain the transmittance spectrum relating virtually only to the transmission spectrum of the sample.

This spectrum stored in the instrument or in a computer connected thereto is stored as a number of transmittances in a number of channels positioned equidistantly on the frequency axis. This spectrum includes points representing discrete points on the actual continuous transmittance spectrum of the sample.

From the manufacturing plant, the instrument or a computer connected thereto has been loaded with a digitized transmittance spectrum (reference pattern) of a standardization liquid and information relating to the positions of two absorptions of the liquid for use in the present standardization.

The reference pattern is preferably obtained from a transmittance spectrum of the standardization liquid performed on a randomly selected instrument of the type to be standardized. Thus, the standardization will be to the actual state of this instrument at the time when the measurement of the transmittance spectrum took place.

In the present context, the standardization liquid includes water and propanol (3.83 w/w% of propanol).

In order to standardize the instrument, the standardization liquid is in the present example introduced in the instrument in the same manner as a typical sample and, thus, into the measuring cuvette where a typical measurement of the transmittance spectrum T of the liquid is performed.

The transmittance spectrum T is subsequently compared to the reference pattern in order to obtain standardization parameters for the correction of subsequent transmittance spectra of unknown samples.

The present standardization liquid is chosen due to it having two well defined absorption peaks in the frequency range in which the present instrument is able to perform measurements: 1000–5000 $cm^{-1}$. These absorption peaks are easily identifiable in the transmittance spectrum of the standardization liquid as two local minima.

In the following, the actual standardization will take place on the basis of the negative transmittance spectrum -T of the standardization liquid, as it is intuitively more easily understandable to compare positions of absorption peaks than local minima in the spectra. Using the negative transmittance spectrum -T, the local minima in the spectrum T caused by absorption of propanol will be transformed into absorption peaks.

First, the peak positions of these two absorption peaks are identified. These positions will typically be positioned close to the positions of the corresponding peaks of the reference pattern. This means that the approximate positions are known from the beginning of the process.

From FIG. 1, the negative transmission spectrum -T (which has similarities with the actual absorbance spectrum) of the standardization liquid in the vicinity of the first absorption peak (denoted by an arrow) may be seen. It may be seen that a long slope is present on one side of the peak (the right side), which means that the peak may be identified by traversing this part of the spectrum -T from the right side of a position from which one is certain that the peak is positioned on the left side. In this manner, the first local maximum detected will typically be this peak.

However, as the spectrum -T will typically contain a certain amount of noise, a number of small local maxima may be present along the slope. This means that a method should be used for the identification of the peak which is not distracted by these smaller local maxima.

In order to further enhance the resolution of the determination of the actual position of the peak, the resolution of the obtained spectrum of the standardization liquid may be increased. Naturally, this may be obtained by performing a scan with a higher resolution of the liquid. In an FTIR instrument, this may be obtained by performing a wider scan over the interference peak.

However, in the present context, it is sufficient that the "higher resolution" results in "more measuring points" in the spectrum. This may be obtained by the method generally known as zero-filling, wherein the short scan taken by the FTIR instrument is mathematically "prolonged" by a number of sampling points all defined to be zero. This does not introduce additional information in the spectrum of the liquid nor is any noise reduced, but the operation results in the spectrum of the liquid having more points along the continuous curve being that ideally determined by the Fourier transformation of the zero-filled interference signal measured by the interferometer.

In the present example, an interference signal scanned using 8 k (8192) points is zero-filled to a total of 32 k. This means that the spectrum of the liquid will contain four times the points of the spectrum of the original interference signal. This "higher-resolution" spectrum will give a better estimate of the position of the peak positions (See e.g. FIG. 2 where the points positioned on natural numbers relate to the original points and where the other points (positioned on ¼, ½ and ¾) are additional points introduced by the zero-filling).

The presently preferred method is one in which, for each point relating to a channel in the spectrum, the nearest 5 points on each side of the point—that is, a total of 11 points centered on the point in question—a 3rd degree polynomial is fitted to the curve described by these points.

It is then checked whether the channel number corresponding to the root of the first derivative of the polynomial having the largest value is positioned within the 11 points in question, this channel number is real (an imaginary channel number can not be used in the present context; The process will, thus, simply carry on until a real channel number is detected) and the value corresponding to the identified channel number is the global maximum of the polynomial within the 11 points in question.

In this manner, the small deviations of the curve generated by noise are eliminated, and the first maximum fulfilling the criteria will be the peak searched for. It should be mentioned that the actual position of the peak will usually be between two channels.

Once this "approximate position" of the peak has been identified, it is presently preferred to fit a second 3rd degree polynomial to the 4 points constituted by the two nearest points on either side of the above peak position. FIG. 2 illustrates the four points on which the polynomial is based, and the identified position of the peak (shown as a circle).

It should be noted that, as the maximum of the polynomial will most probably not be positioned in one of the points fitted by the polynomial, the identified position of the peak will usually not coincide exactly with the points of the spectrum. This, however, has no impact on the standardization. The primary target of this operation is to precisely identify the position of the peak.

In accordance with the above method of identifying the position of peak 1 (FIG. 1), peak 2 (FIG. 3) is determined in the same manner. From FIG. 3 it is seen that the best way of identifying the position of this peak is to start from the opposite side of that of/the above method. Apart from that, the methods of identifying the positions of the peaks are identical.

As FTIR instruments inherently are very similar, the differences between two spectra of the same sample measured by two different FTIR instruments will mainly be generated by a relatively few and well defined causes of which the most predominant are:

a) a difference in sample cuvette thickness which will give a difference in the amount of light absorbed in the cuvette and sample, b) a difference in wavelength of the two lasers in the interferometers which will give a shift on the frequency axis of the final spectra, and c) a difference in the alignment of the IR light and the laser light in the interferometer will also give a shift on the frequency axis of the final spectra.

Re. a), a different thickness of the sample cuvette may be both a different thickness of the material constituting the sample holding cuvette and a different thickness of sample, defined as the distance between two opposite cuvette windows, which the light must pass. In both instances, the difference may be caused by wear of the cuvette. In fact, cuvette materials such as CaF are slightly hygroscopic, whereby the sample cuvette may actually be slightly dissolved during measurement of aqueous samples, such as milk samples. This process, however, is quite slow so that a CaF cuvette may be used for one year and for measurement on 200,000–400,000 samples.

According to Lambert-Beer's law, this difference will give a linear scaling of the absorbance axis of the measured spectrum.

Re. b), the Fourier transformation used in FTIR instruments requires that the interference signal produced in the interferometer and detected by the detector is scanned equidistantly as a function of the difference in light path, such as being the movement of a movable mirror. In typical FTIR instruments this is ensured by launching laser light into the interferometer and by trigging the measurements of the interference peak on, e.g., a phase lock of the laser light or on zero-crossings of the interfering laser light in the interferometer.

In this situation, a difference in laser light frequency will cause two different instruments to trigger the measurements of the interference pattern equidistantly at slightly different distances. Thus, this will give a difference on the frequency scale of the measured spectrum.

Due to the above, however, this difference will be a linear scaling of the frequency axis of the spectrum. As the Fourier transformed spectrum will be constituted of a number of equidistant points on the frequency axis, the distance of these points will be different from instrument to instrument. However, in order to correct this, the "ruler" constituted by the equidistant frequencies should merely be compressed or stretched. No non-linear effects will typically be generated in this process.

The same effect will be seen when other distance measuring means are used in this type of instrument. This is given by the Fourier transformation taking place.

A frequency shift will be seen when the IR light in the interferometer does not follow exactly the same path as the laser light. In this situation the interference signal of the interfering IR light will be trigged equidistantly, such as on zero-crossings of the interfering laser light, but with a different distance compared to the situation where the laser light exactly overlaps the IR light. Thus, the "ruler" of the equidistant trigging will not be that of the laser wavelength but slightly shifted so that the above stretching or compressing of the "ruler" will still correct the frequency axis.

This adaption of the frequency axis may be performed on the basis of the identified positions of the two absorption peaks of the propanol in the standardization liquid, when the positions of these peaks of the reference pattern are known.

FIG. 4 illustrates the best straight line drawn through the three points constituted by on the x-axis the peak positions (channel number) of spectrum -T and on the y-axis the difference, in channel number, between the peak positions of spectrum T and that of the reference pattern, and origo.

It is seen that the assumption that the difference is a linear scaling of the frequency axis may be retained. From this figure, the frequency shift which will transfer any channel from the measured spectrum into the corresponding channel of the reference pattern may be derived.

Thus, as this shift may be described by a formula of the type:

$$Shift = \alpha \cdot channel + \beta$$

only two variables ($\alpha$ and $\beta$) are required in order to correct the frequency axis of future spectra in order to standardize this axis. In fact, as $\beta$ is substantially zero, only $\alpha$ is required if a slightly smaller precision is sufficient.

However, as the measured spectrum includes discrete points illustrating the actual transmittance spectrum of the sample, the shifting of the frequency axis of this spectrum requires re-calculation of the points of the new, shifted spectrum.

This re-calculation is illustrated on FIG. 5 wherein a simulated curve is shifted according to the above formula using $\alpha=0.1$, $\beta=0$. The original spectrum is shown in a full line and the corresponding shifted spectrum is shown in a broken line.

For each channel of the original spectrum, the shift is calculated from the above formula. For channel 6, e.g. the shift is 0.6. This means that channel 6 should have the transmittance of the original spectrum at the position of 6.6. As the original spectrum has no such channel, this value has to be calculated. To this effect, a 3rd degree polynomial is fitted to the two nearest points on either side of the shifted position. This means that channels 5, 6, 7 and 8 are used for position 6.6.

On the basis of this polynomial, which now describes a continuous curve approximating the actual part of the spectrum, the transmittance value at the shifted position may be calculated. In this manner, the new points for the shifted spectrum may be calculated.

Performing this operation on the spectrum T, the frequency axis of the shifted, measured spectrum T' will now coincide with that of the reference pattern.

The interpolation methods used above may naturally be of any suitable type such as a cubic, as described above, Gregory-Newton, Everett, Lagrange or quadratic interpolation.

In accordance with a) above, also the transmittance axis should be corrected. This correction may most simply be corrected on the basis of the transmittance difference between only a single channel of the spectrum, such as the transmittance difference in one of the identified peaks in the spectrum T and the reference pattern, and on the basis of the assumption that the correction is a linear correction (linear in absorbance being the $-\log_{10}$ of transmittance—see below) throughout the part of the spectrum which is interesting for the present purpose. In this case, the only information of the reference pattern (spectrum of the standardization liquid as determined initially) that is required at all is the channel numbers and transmittances in which the two identified peaks of the shifted spectrum T' should be positioned when standardized. Thus, the reference pattern required for this simple standardization is simply the peak points of the two peaks.

However, due to the interference of e.g. noise, it is presently preferred to use a larger number of values in selected ranges in order to reduce the probability of error in the calculation.

Due to the above assumption that the correction of the absorbance axis will be a linear scaling in absorbance values, a correction of the below type is assumed:

$$T_{reference} = b \cdot T^{\prime a}$$

From the consideration that, in order to transform a transmittance spectrum into an absorbance spectrum, the negative logarithm should be taken to the transmittance spectrum, it is seen that this will give a linear correction of the absorbance axis of the spectrum.

$$\log_{10}(T_{reference}) = a \cdot \log_{10}(T') + \log_{10} b$$

which means that a and $\log_{10} b$ may be found.

That a factor should be multiplied to the absorbance value follows from Lambert-Beer's law.

Thus, a and $\log_{10} b$ may be found by plotting, on one axis, the logarithm to the frequency shifted spectrum T' and, on the other axis, the logarithm to the reference pattern. From this plot, which again results in a substantially straight line (See FIG. 6), the best straight line through all points is found, using an ordinary Least Squares Fit, and the variables a and $\log_{10} b$ calculated. Again, $\log_{10} b$ is close to zero and may be omitted if a less precise standardization may be sufficient.

Thus, from the above, the variables $\alpha$, $\beta$, a and b are found. These variables will subsequently be stored in the instrument or a computer linked thereto in order to correct subsequent spectra of unknown samples in order to standardize these spectra.

The standardization of a transmittance spectrum of an unknown sample will be performed in accordance with the above, where a frequency shifted spectrum T' will first be generated which will then be entered into the following formula:

$$T_{standardized} = bT^{\prime a}$$

in order to generate the standardized spectrum.

In the present example, a large water absorption is positioned between the above-mentioned two peaks, whereby the frequency range in this absorption cannot be used for the correction of the y-axis. Thus, it is presently preferred to exclude this frequency range and limit the channels used in the above plot to only those suited for that use. For other systems there may be other reasons for excluding frequency ranges for this use.

However, if the exactness of the standardization was to be increased, one might wish to be able to correct for 2nd order effects such as if the emission of the light emitter was not linearly shifted but some wavelengths gained in intensity and others not. The same applies to changes in the sensitivity of the detector.

If the correction of the absorption axis was not a simple linear correction, there are multiple ways to standardize a spectrum. In the situation above, where a water absorption is positioned in the spectrum, and if this is also the situation in the spectra to be standardized, the transmittance correction may be performed for each "window" between the water absorptions. As these windows will be relatively smaller that the full spectrum, the correction may with success be assumed to be linear in each window, whereby different a's and b's may be found for each window.

This method may give rise to non-continuities in the full spectrum if no water absorptions are present in this spectrum. This effect may be removed by, instead of the above, accepting that the correction is not homogeneous and instead determining individual a's and b's for each channel in the frequency-corrected spectrum.

This may be achieved by performing the operation described in connection with FIG. 6 for the point relating to the channel in question and e.g. the two nearest points on each side and, thus, obtaining an a and a b for this separate channel.

Subsequently, two different polynomials may be fitted to the a's and the b's, respectively. These polynomials will then be used for the transmittance correction instead of the above global a's and b's.

A third method is to simply fit a polynomial to the difference or ratio of the transmission of the frequency corrected spectrum and the reference pattern. This polynomial may thereafter be used to standardize the absorption axis of a spectrum.

EXAMPLE 2

Interchangeability of calibrations

In the present example, a standard calibration for the determination of fat in milk is developed on a first instrument, in the following denoted the reference instrument, and transferred to another instrument, called the slave instrument. Due to the standardization, the calibration developed on one instrument may be directly used on other instruments. The purpose of the present example is to evaluate the degradation of the prediction of the concentration of fat caused by differences on the frequency and absorption scales compared to predictions based on standardized spectra ($T_{standardized}$—See Example 1).

The present calibration describes the connection between the concentration of fat in the sample and the absorbance determined in a number of selected wavebands. In the present example, the following wavebands, which are typical for IR determination of fat in milk, were selected:

|      | Channel No. | B Coeff.* | $D_f$    |
|------|-------------|-----------|----------|
| L    | 270–274     | −2.4602   | 0        |
| TS   | 296–302     | −0.6829   | 0.00507  |
| FC   | 376–380     | −0.0032   | −0.05502 |
| P    | 395–399     | 2.4692    | 0        |
| FA   | 448–452     | 4.2055    | 0.12281  |
| FB   | 736–742     | 12.7845   | 0.06241  |
| $P_{ref}$ | 384–388 |           |          |

Constant: 0.0206

*determined as a PLS-determination

In the present instrument, the frequency (in cm$^{-1}$) may be found from the channel number by multiplying by approximately 3.86.

When determining the concentration of fat in milk, a mean value of the transmittance in each of the above channel intervals is determined.

The $D_f$ values are used for linearization of the signals due to the effect that the Lambert-Beer law is only valid for small concentrations of e.g. fat. At higher concentrations, the signal will not be linear. However, using the below linearization the signal will be linear also for higher concentrations.

This mean transmittance value is transformed into an absorbance value by taking the negative logarithm to this mean value.

For the first 6 wavebands the mean transmittance thereof is divided by the transmittance in the reference waveband ($P_{ref}$) as a typical reference waveband. Thereafter, the linearization is performed. The formula describing this is:

$$absorbance = -\log_{10}\left(\frac{\frac{T_{sample}}{T_{reference}} - D_f}{1 - D_f}\right)$$

Naturally, also other types of linearization may be used, e.g. 2nd order polynomials.

Finally, the B coefficient is multiplied to this absorbance for all 6 wavebands and these results and the Constant are finally added to give the predicted concentration of fat in the sample.

In instruments typically used for infra red determination of e.g. fat in milk, the user frequently performs an operation called Slope/Intercept correction in which systematic variations of the predicted value of fat are corrected.

The most important reason for performing a Slope/Intercept operation on a spectrometer is that the calibration may not be made taking into account the actual chemical reference method used by the laboratory using the spectrometer in question. As different laboratories in different countries use different reference methods for determining fat in milk, the calibration may not correspond exactly to this reference method, if the calibration is developed using a different reference method. A Slope/Intercept operation will remove this difference, as the different reference methods give systematically varying determinations of fat in milk.

In addition, this type of instrument drifts with time, whereby also the predicted value of e.g. fat will drift. A Slope/Intercept operation will correlate the calculated fat concentration and the "true" fat concentration in order to correct the concentration calculated on the basis of the calibration.

Furthermore, a Slope/Intercept operation will take into account a variation in the performance of e.g. a homogenizer acting on the sample before the measurement. A difference in the degree of homogenization of a milk sample will give a difference in the size distribution of the fat globules in the sample again giving a different degree of absorption and scattering of these globules.

The Slope/Intercept operation comprises introducing a number of samples into the instrument and at the same time informing the instrument of the actual concentration of fat in the samples as determined by the chemical reference method. On the basis of this, the instrument calculates a curve much like the curve on FIG. 7 where the correct value for the predicted fat may be determined on the basis of the calculated value. This operation corrects the calculated values when the measured spectrum and the calibration no longer cooperate to give correct predicted values.

This operation seemingly performs part of the task taken care of by the standardization according to the invention, as it corrects the calculated concentrations.

However, even though the above operation "cures the symptoms" that the calibration does not result in correct predicted values, the standardization according to the invention "cures the disease" by correcting the measured spectrum so that the calibration results in correct predicted values.

In addition, the frequency shift performed in the standardization of the present invention is not performed during a Slope/Intercept operation. This means that the frequency differences between the instruments are not corrected by this operation. This has only little effect in the present example, as the wavebands used in the present calibration are quite broad, whereby a relatively large frequency shift may still result in acceptable results. However, in other calibrations using more narrow absorption peaks, the above Slope/Intercept operation will not be able to correct the calculated concentrations.

Thus, the standardization of the invention takes over part of the corrections performed by the Slope/Intercept operation. This is highly desired, as the Slope/Intercept operation only performs an approximate correction, where the standardization according to the invention performs a more correct and thorough correction. In fact, the Slope/Intercept operation is incorrect when, as a matter of fact, a correction of the frequency axis has to be performed.

On the other hand, as the present standardization only takes into account differences in the light path of the instrument, the Slope/Intercept operation complements the standardization, as it also takes into account other effects, such as differences in reference methods and the state of a homogenizer. Thus, the optimal use of these operations will be to firstly standardize the instrument, in order to have the standardization perform a correction of the effects in the light path, and subsequently have a Slope/Intercept operation correct the instrument for the effects taken into account by this operation and not by the standardization.

In the present example, the fat concentration is predicted for a number of samples on both the reference instrument (Reference), the slave instrument without neither standardization nor Slope/Intercept (Slave), the slave after standardization without Slope/Intercept (Slave (std)), the slave before standardization and after Slope/Intercept (Slave (S/I)) and the slave instrument after both standardization and Slope/Intercept (Slave (std/S/I)).

The predicted concentrations are given in the below table.

| Reference | Slave | Slave (std) | Slave (S/I) | Slave (std/S/I) |
|---|---|---|---|---|
| 0.07 | 0.00 | 0.06 | 0.05 | 0.07 |
| 1.92 | 1.79 | 1.92 | 1.93 | 1.93 |
| 2.43 | 2.28 | 2.42 | 2.44 | 2.43 |
| 2.92 | 2.75 | 2.91 | 2.93 | 2.92 |
| 3.36 | 3.16 | 3.35 | 3.37 | 3.36 |
| 3.83 | 3.59 | 3.80 | 3.82 | 3.81 |
| 3.97 | 3.72 | 3.94 | 3.95 | 3.95 |
| 4.16 | 3.92 | 4.15 | 4.16 | 4.15 |
| 4.27 | 4.02 | 4.25 | 4.26 | 4.26 |
| 4.35 | 4.11 | 4.35 | 4.36 | 4.36 |
| 4.39 | 4.14 | 4.38 | 4.39 | 4.39 |
| 4.43 | 4.18 | 4.42 | 4.43 | 4.43 |
| 4.54 | 4.28 | 4.53 | 4.54 | 4.54 |
| 4.73 | 4.47 | 4.72 | 4.73 | 4.73 |
| 5.93 | 5.60 | 5.94 | 5.92 | 5.94 |
| SEP |  0.067 | 0.009 | 0.010 | 0.009 |
| Slope | 1.000 | 1.000 | 1.049 | 0.999 |
| Intercept | 0.000 | 0.000 | 0.048 | 0.011 |

Thus, even though, for the above reasons, the results of a standardized slave instrument (SEP-std), a slave (SEP-S/I) having been Slope/Intercept-corrected and a slave being both standardized and Slope/Intercept corrected (SEP-std-S/I), are comparable, it is seen that the Slope and Intercept values of standardized instruments are much closer to 1 and 0 which means that the standardization is the only correction required of the slave instrument in order to facilitate transfer of the calibration.

EXAMPLE 3

A preferred interferometer for the present invention

FIG. 8 illustrates the basic structure of an FTIR spectrometer for use in IR spectrometry and comprising a typical Michelson interferometer 2 comprising a stationary mirror 4, a moving mirror 6 and a beam splitter 8 with a corresponding compensator plate 10. An IR light emitter 12 launches collimated IR light into the interferometer 2 via a collimating mirror 14, and interfering IR light emitted from the interferometer 2 is launched through a sample cuvette 16 and onto a light detector 20 via a focusing mirror 18.

The interference signal produced in the interferometer 2, due to the movement of the moving mirror 6 causing the optical path length of one of the optical paths in the interferometer 2 to vary compared to that of the other path, is preferably detected at a equidistant points along the movement of the moving mirror 6, in order to be able to Fourier transform the scanned interference signal. If a standard Fourier transform algorithm is used on a scanned interference signal in which the scanning points are equidistant in the movement of the moving mirror 6, the resulting spectrum will be represented by points equidistant in frequency.

The compensator plate 10 compensates in a manner known per se for the dispersion of the substrate of the beam splitter 8.

In the art, a number of methods have been used in order to facilitate this equidistant triggering or scanning of the IR-interference signal as a function of the movement of the moving mirror 6. One way of facilitating this equidistant triggering is to launch light emitted from a laser 24 into the interferometer 2, whereby the laser light, also interfering in the interferometer 2, will create an interfering fringe pattern, which may be detected by an additional detector 26.

The presently preferred interferometer has:

A light emitter of the temperature emitter type having a light emitting area of a diameter of 4.5 mm. This type of light emitter may be manufactured from a thin conductor or semiconductor (such as an oxide-semiconductor) heated when a current is fed therethrough and which, when heated, emits light. Another type of light emitter is one comprising a coaxial setup where the current is fed through the inner conductor and where the outer conductor is heated by the inner conductor so as to emit the light.

A light detector typically of the quantum detector type or the thermoelectric type such as a thermoelement, a Golay cell, a bolometer or a pyroelectric type, such as a DTGS or a Lithium tantalate detector.

The preferred characteristics of the optical setup are:

Focal length of light source mirror 14: 36 mm
Focal length of detector mirror 18: 18.75 mm
Diameter of interferometric mirrors 4,6: 25.4 mm
Diameter of beamsplitter 8: 25.4 mm
Beamsplitter material ZnSe, ZnS, Ge etc.

Preferred dimensions are (from center of the beamsplitter):

Distance between mirror 14 and beamsplitter 8: 75 mm
Distance between beamsplitter 8 and mirror 4: 22 mm
Distance between beamsplitter 8 and mirror 6: 22 mm
Distance between beamsplitter 8 and mirror 18: 80 mm A setup of this type gives a divergence angle in the interferometer of 3.6°. This large divergence angle is optimal for the main purpose of the preferred interferometer: the determination of the constituents of liquid and especially aqueous samples.

As the absorption peaks in this type of samples are typically broader than those of e.g. gasses, the frequency resolution of the interferometer need not be as high as for instruments performing determinations on gasses.

Due the presence of water in the samples, the total absorption of the sample is high, whereby a large amount of light is required in order to be able to perform the determination. To this effect, the large angle of divergence, allows more light to be launched through the cuvette, whereby also a thicker cuvette may be used. Thicker cuvettes may be desired, as these are typically easier to clean after use.

Due to the large absorption of water, it is desired to have a thin cuvette. On the other hand, a thicker cuvette is desired from the point of view of ease of cleaning the cuvette.

In standard filter instruments for analysis of milk, such as the MilkoScan instruments from Foss Electric, a cuvette thickness of 37 $\mu$m is typically used. A cuvette thickness of this size will also be convenient in an instrument according to the present invention when determining the concentrations of the constituents of milk. However, also cuvette thicknesses down to 10 or 20 $\mu$m and thicknesses of up to 50 or 100 $\mu$m may be convenient depending on the sample and the absorptions of the sample. In fact, at present, a cuvette thickness of 50 $\mu$m has been found quite satisfactory when determining the concentrations of constituents of milk.

As instruments of this type are typically positioned at positions where vibrations may occur, the above preferred compact setup will render the instrument less sensitive to vibrations compared to setups having larger light paths.

In FIG. 9, laser light from the additional laser 24 is directed into the interferometer 2 and extracted from the light output therefrom and directed onto a detector 26 by mirrors 28 and 30. Naturally, this manipulation of the laser light may be performed in a number of other ways.

As e.g. a HeNe laser is typically monochromatic, the interfering light from the light source 12 may be detected each time a zero crossing of a fringe or a certain number of fringes are detected by the detector 26 in order to facilitate this equidistant scanning of the interfering IR light.

An optional manner of obtaining an equidistant detection of the IR-interference signal is to directly detect the position of the moving mirror.

A number of different means may be provided for performing the actual translation of the moving mirror 6. In the present instrument, it is preferred to utilize a principle basically known from loudspeakers wherein an electrical current is introduced in a coil positioned in a static magnetic field, whereby the coil moves in accordance with the force generated by the introduced current.

The presently preferred driver for the moving mirror may be seen from FIG. 10, wherein the moving mirror 6 and the holder therefor (assembled denoted 40) is attached to a main frame 42 on which a drive coil 44 is also mounted. The drive coil 44 is positioned within a magnetic field created by a static magnet 46 mounted in relation to the base plate 48. The field lines of magnet 46 are transferred to the coil 44 through elements 47, 49 and 51, respectively, where elements 47 and 51 are of soft metal and 49 is of a nonmagnetic material.

In order for the frame 42 to be able to be translated in relation to the base plate 48, the frame 42 is mounted on flat springs 50 mounted in a manner so that the frame 42, the drive coil 44 and the moving mirror and holding means therefor 40 may be moved in a direction substantially perpendicular to the plane of the moving mirror 6, and so that movement in the plane of the moving mirror 6 is substantially prevented.

In the most simple solution, one may choose to rely on simply supplying the drive coil 44 with suitable electric current and maybe additionally using the laser fringes from the interferometer 2 in order to determine the position of the mirror 6 so as to obtain equidistant scanning of the interference signal in the interferometer 2.

However, it is often desired to be able to more directly monitor the velocity of the moving mirror 6. One way of obtaining this monitoring is to use a phase-locked loop (PLL) as known per se in which a feedback loop is locked to the phase of the interfering laser light in the interferometer 2.

The frequency of the interfering laser light is compared to a reference frequency defining the desired velocity of the mirror 6. In this manner, the velocity—or rather any deviations from the reference velocity—may be observed.

However, using this monitoring, the velocity of the mirror 6 is typically only determined in discrete steps corresponding to a displacement of the mirror 6 of ¼ wavelength of the laser light.

In fact, the results of the PLL may be adapted to be either fast or steady. This is due to the PLL typically incorporating an integrator integrating the output of a multiplication circuit (e.g. an XOR gate) having as input the reference frequency and the detected frequency from the laser detector. Obtaining steady results requires the integration to be performed over a longer period, whereby obtaining the results takes a relatively longer time.

However, as the above method merely provides information concerning discrete points along the movement of the moveable mirror 6 and as the method is relatively slow, it may be desired to further monitor the velocity in order to obtain faster and more continuous information thereof.

This may be obtained using a principle similar to that of the driver, wherein an electrical coil is moved in a stationary magnetic field.

In the preferred driver seen in FIG. 10 for the movable mirror 6 in the present interferometer 2, this monitoring is provided by two electrical coils 52 and 54 connected in counter-phase so that the windings of one are inverted compared to those of the other, and wherein each coil is introduced in a static magnetic field provided by the magnet 56 mounted in relation to the base plate 48.

The magnet 56 is along the axis of the driver contacted by two pieces 57 of soft metal which transfer the field lines of the magnet 56 to the inner side of the coils 52 and 54 and through a circular element 58 of brass to a circular piece of soft metal 59 which transfer the field lines of the magnet 56 to the outer side of the coils 52 an 54. The reason for using a non-magnetic material as the element 58 is the fact that a magnetic material would short circuit the field lines of the magnet 56.

The reason for this inverted setup is that any influence from external magnetic fields will then be substantially compensated for.

In order to reduce the effects of external magnetic fields, the sensing coils 52 and 54 are preferably enclosed in a protective casing of $\mu$-metal.

The difference between the Phase-Locked Loop (PLL) and the velocity servo of FIG. 10 is, as is described above, that the PLL only generates information concerning discrete points of the velocity of the moving mirror 6, whereas the velocity servo of FIG. 10 generates continuous information. In addition thereto, the velocity servo is typically faster than the PLL.

Thus, these two methods may be used either one at the time or they may both be used, as they complement each other.

In fact, it is contemplated that a combination of the phase locked loop and the electrical velocity servo may provide an extremely well-functioning monitoring of the velocity of the movable mirror. In addition, the monitoring signal from these servos may be fed back to the controlling electronics (not shown) feeding the drive coil 44 in order to have a regulation of the velocity of the moving mirror 6. This may act in preventing or reducing the effects caused by vibration a.s.o. of the instrument.

Naturally, if one merely requires a less precise determination of the velocity of the mirror 6, the instrument may, in fact, work satisfactorily without monitoring functions of the velocity of the mirror 6.

As is described in the applicants co-pending patent application Ser. No. PCT/DK95/00492, the time delays caused by filters 76 and 74 connected to the detector 18 detecting the IR interference signal and the additional detector 26 detecting the interfering laser light, respectively, are not identical. Thus, the trigging of detection of the interfering IR light should not take place when a laser fringe is detected but shortly thereafter.

As is described in the applicants co-pending application, this delay may cause certain problems, whereby it is presently preferred to introduce delay electronics 70 between the filter 74, filtering the electrical signals from the detector 26, and the sampling electronics 72 typically employed. Introduction the delay electronics 70 will ensure that the trigging of the IR light will take place according to the detected laser fringes.

Depending on the actual use of the instrument according to the present invention, it may be preferred to insure that the surroundings of the interferometer 2 and especially the atmosphere surrounding the light travelling in the interferometer 2 is kept constant.

In instruments using infrared light for quantitative or qualitative determination of components in e.g. milk, it is highly preferred that as little as possible or at least a constant amount of water vapour is present in the path of the IR light, as this vapour will absorb part of the light and thereby effect the results. Thus, in the preferred instrument for use in performing measurements on milk, the interferometer 2 is positioned within a substantially airtight casing 80 which is thermostated and dried out using e.g. silicate gel as is known in the art.

In FIG. 11, the surroundings of the interferometer 2 are illustrated.

For the long-term stability of an instrument, it is important that no thermal gradients are present therein, as a thermal gradient may produce deformation etc. of the individual elements. Thus, it is presently preferred that the entire casing 80, wherein the interferometer 2 (not shown) is positioned, is thermostated. In the present instrument, a heating element 82 is positioned in a rod 86 mounted on the base 92 of the casing 80. The rod 86 protrudes through an aperture 94 in a base plate 90 on which the interferometer 2 (not shown) is mounted.

This base plate 90 is preferably mounted on flanges 88 positioned close to the aperture 94; these flanges 88 preferably constitute the only support of the base plate 90 and the only physical contact between the base plate 90 and the base 92.

When the heating element 82, which constitutes a part of a thermostating unit (not shown), is positioned in the rod 86 and when a temperature sensor 84 of the thermostating unit is also positioned in the rod 86 close to the intersecting point between the rod 86 and the base plate 90, this intersecting point will be well thermostated. Thus, as the only physical contact between the casing 80 and the base plate 90 is the flanges 88 positioned close to the temperature sensor 84, also the base plate 90 will be well thermostated.

In addition, as the rod 86 is preferably in thermal contact with the casing 80 comprising the interferometer (not shown), also the casing 80 is thermostated. Thus, using the presently preferred setup shown on FIG. 11, a well thermostated optical unit is obtained.

Depending on the actual sample to be introduced into the optical path of the instrument, and other considerations connected thereto, the actual optical setup of the instrument may be varied.

Thus, in the presently preferred instrument, which is primarily targeted for determination of components in milk, it is presently preferred not to have the sample cuvette 16 positioned within the casing 80, where it would be positioned close to the optical elements (e.g. 4, 6, 8, 10) of the interferometer 2. A relatively high pressure may be introduced into the sampling cuvette 16, whereby breakage thereof might otherwise contaminate the optical elements of the interferometer 2. In addition, it is preferred also to position the light emitter 12 outside the thermostated casing 80, as the light emitter 12 typically emits relatively large amounts of heat; this may reduce the accuracy of the thermostating of the interferometer 2.

In order to transmit the light from the light emitter (not shown) to the interferometer 2 in the casing 80, at present a simple hole is provided between the casing 80 and an enclosure (not shown) enclosing the light emitter and being thermally isolated from the casing 80.

In the present instrument, the two mirrors 4 and 6 and the beam splitter 8 of the interferometer 2 are mounted by contacting these optical elements in only three points. This feature, which is known per se, tends to reduce the tension in these optical elements and, thus, the flexing thereof, which might otherwise create problems.

In a number of the known interferometers in which a laser beam from a laser is used for the equidistant trigging of the interfering IR light and where the laser beam and the IR light in the interferometer overlap in the interferometer, the beamsplitter should be able to split both the IR light and the laser light. In order to obtain this splitting, typical beamsplitters for this use typically have different coatings at the center thereof for splitting the smaller-diameter laser beam, and at the more peripheral parts thereof for splitting a major part of the larger-diameter beam of IR light. In a standard beamsplitter having a diameter of eg 45 mm, the laser beamsplitter typically has a diameter of eg 10 mm.

Thus, it is not possible to totally overlap the laser beam and the IR light in the interferometer 2; at present, the laser beam is positioned in the upper part of the optics of the interferometer 2. Thus, in a beamsplitter having a diameter of eg. 25.4 mm (1 inch), a horizontally outlined part constituting e.g. 4 mm of the diameter of the beamsplitter may constitute the laser beamsplitter.

We claim:

1. A method for standardizing a spectrometer generating an optical spectrum from a sample, wherein the optical spectrum comprises a frequency range wherein the spectrometer is to be standardized, the method comprising:

generating at least one optical spectrum from at least one standardization sample each having a chemical composition resulting in the optical spectrum showing localized characteristic patterns in one or more predetermined frequency ranges, the one or more frequency ranges covering only one or more localized parts of the frequency range to be standardized, comparing information relating to the characteristic pattern(s) to corresponding information relating to reference pattern(s) previously defined as the desired standard response(s) for the at least one sample, utilizing the comparison of the information and a proportional frequency compression/expansion model predicting, on the basis of deviations between information in the individual pattern(s) of the generated spectrum or spectra from that of the corresponding reference pattern(s), transformation of parts of the frequency range to be standardized not being in the one or more predetermined frequency ranges to determine standardizing parameters defining transition of the pattern(s) of the generated spectrum or spectra to the reference pattern(s) and of the remainder of the frequency range to be standardized, storing said standardizing parameters in the spectrometer or a computer connected thereto, and in the spectrometer using the stored standardizing parameters for generating, when presented with an unknown sample, a standardized optical spectrum substantially identical to that which would be generated in a corresponding spectrometer standardized with at least one standardization sample of the same chemical composition(s) using the same previously defined reference pattern(s), wherein no additional optical elements are introduced in the light path, the effect of which elements introduces an additional effect which is not present when performing measurements on normal samples.

2. A method according to claim 1, wherein the standardization sample is introduced and handled in the spectrometer in the same manner as unknown samples to be measured are introduced.

3. A method according to claim 1, wherein the spectrometer is a spectrometer which generates a continuous spectrum.

4. A method according to claim 3, wherein the spectrometer is a spectrometer which employs Fourier transformation.

5. A method according to claim 1, wherein the optical spectrum is an absorption spectrum or a transmission spectrum.

6. A method according to claim 1, wherein the optical spectrum is an emission spectrum.

7. A method according to claim 1, wherein the spectrometer is a spectrometer adapted to handle liquid samples, and the standardization sample is a liquid sample.

8. A method according to claim 1, wherein the characteristic pattern(s) comprise(s) one or more local maxima or minima in the optical spectrum or in one of its derivatives.

9. A method according to claim 8, wherein the characteristic pattern(s) comprise(s) one or more local maxima or minima in the optical spectrum positioned at fixed frequencies on the frequency axis of the spectrum.

10. A method according to claim 9, wherein the fixed frequencies are frequencies characteristic to the identity of one or more chemical constituents of the standardization sample.

11. A method according to claim 10, wherein the chemical composition of the standardization sample is one which is within such concentration tolerances that the fixed frequencies are unambiguously identified by the local maxima or minima.

12. A method according to claim 11, wherein the standardization sample is stable after storage at 20° C. in a sealed container for at least 1 year after the production and packing of the sample.

13. A method according to claim 12, wherein the standardization sample is stable after storage at 20° C. in a sealed container for at least 2 years after the production and packing of the sample.

14. A method according to claim 1, wherein the components of the standardization sample(s) the identity of which is decisive to the frequencies of the local maxima or minima are selected from mixtures of water and lower alcohols.

15. A method according to claim 14, wherein the components are constituted by a mixture of water and propanol.

16. A method according to claim 15, wherein the mixture is a mixture of water and propanol having a concentration of propanol in the range of 1–5% w/w, the concentration being within a tolerance of ±10% relative.

17. A method according to claim 1, wherein the concentrations of the components of the standardization sample(s) is/are kept within such tolerances that any error on the amplitude axis of the spectrum ascribable to concentration variations in the standardization sample is less than the repeatability of the spectrometer.

18. A method according to claim 1, wherein the comparison of the information relating to the measured pattern(s) to corresponding information relating to the reference pattern(s) comprises identifying the frequencies in the measured pattern(s) at which local maxima or minima corresponding to local maxima or minima in the reference pattern(s) are positioned.

19. A method according to claim 1, wherein the determination of standardizing parameters comprises determining the relation between the identified frequencies in the measured pattern(s) and the corresponding frequencies in the reference pattern(s) and obtaining parameters describing the frequency relation.

20. A method according to claim 19, wherein the generated optical spectrum is transformed using the parameters describing the frequency relation so as to obtain a transformed spectrum in which at least the identified local maxima or minima are positioned at substantially the same frequencies as in the reference pattern(s).

21. A method according to claim 20, further comprising comparing, over at least one frequency range, the amplitude of the frequency-transformed spectrum and the corresponding amplitude of the reference pattern(s) and obtaining standardization parameters describing the relation between the amplitude of the frequency-transformed spectrum and the amplitude of the reference pattern(s).

22. A method according to claim 1, wherein the determination of standardizing parameters comprises determining the relation between the amplitudes of the measured pattern (s) at the identified frequencies and the amplitudes of the reference pattern(s) at the corresponding frequencies and obtaining parameters describing the relation.

23. A method according to claim 22, wherein the relation is described as a linear function of the frequency.

24. A method according to claim 1, wherein the reference pattern(s) is/are derived from a spectrum or spectra generated by a spectrometer on the basis of at least one sample of substantially the same chemical composition(s) as the at least one standardization sample(s).

25. A method according to claim 1, wherein characteristic pattern(s) of the optical spectrum of the at least one standardization sample is/are known or optionally predefined at the time of generating the optical spectrum from the at least one standardization sample.

26. A method according to claim 1, wherein the at least one standardization sample is of a type which is different in chemical composition from the unknown sample.

27. A method according to claim 1, wherein the model assumes an interrelation between the positions on the frequency axis of at least parts of the characteristic patterns of the optical spectrum of the at least one standardization sample and the corresponding parts of the reference patterns.

28. A method according to claim 27, wherein the interrelation assumed is a linear interrelation.

29. A method according to claim 1, wherein the model assumes an interrelation between the positions on the absorption axis of at least parts of the characteristic patterns of the optical spectrum of the at least one standardization sample and the corresponding parts of the reference patterns.

30. A method according to claim 29, wherein the interrelation assumed is a linear interrelation or a first-order interrelation.

31. A method according to claim 1, wherein one or two standardization samples are used.

32. A method according to claim 31, wherein a single standardization sample is used.

33. A method according to claim 1, wherein 1–100, such as 1–80, preferably 1–10, such as 2–5, preferably 2 characteristic patterns and/or reference patterns are used.

34. A method according to claim 1, wherein the one or more predetermined frequency ranges cover not more than 90%, such as not more than 70%, preferably not more than 50%, such as not more than 30%, preferably not more than 20%, such as not more than 10%, preferably not more than 5% of the frequency range to be standardized.

35. A method for obtaining a standardized optical spectrum of an unknown sample, the method comprising measuring an optical spectrum of the unknown sample using a spectrometer which has been standardized using the method of claim 1 and transforming the measured spectrum into a standardized spectrum by applying the standardization parameters obtained from the standardization of the spectrometer and stored in the spectrometer or a computer connected thereto.

36. A method for calibrating a spectrometer which generates an optical spectrum from a sample, comprising standardizing the spectrometer by the method claimed in claim 1 and introducing, into the spectrometer, calibration coefficients established on the basis of measurements performed on one or more other spectrometers which have been subjected to the same standardization.

37. A method according to claim 36, wherein the calibration coefficients have been established on the basis of measurements performed on a single spectrometer which has been subjected to the same standardization.

38. A method according to claim 36, wherein the calibration coefficients have been established on the basis of measurements performed on two or more spectrometers which have been subjected to the same standardization.

39. A method according to claim 36, wherein the calibration has been performed with respect to the prediction of the concentration of one or more components in a given sample type.

40. A method for standardizing a plurality of spectrometers each of which generates an optical spectrum from a sample, wherein the optical spectra include a frequency range wherein the spectrometers are to be standardized, the method comprising:

generating, in each spectrometer, at least one spectrum from at least one standardization sample each having a chemical composition resulting in an optical spectrum showing localized characteristic patterns in one or more predetermined frequency ranges, the one or more frequency ranges covering only one or more localized parts of the frequency range to be standardized, comparing, in each spectrometer, information relating to the pattern(s) to corresponding information relating to reference pattern(s) previously defined as the desired standard response for the at least one standardization sample, utilizing the comparison of the information and a proportional frequency compression/expansion model predicting on the basis of deviations between information in the individual pattern(s) of the generated spectrum or spectra from that of the corresponding reference pattern (s), transformation of parts of the frequency range to be standardized not being in the one or more predetermined frequency ranges, to determine standardizing parameters defining transformation of the pattern(s) of the generated spectrum or spectra so as to correspond to the reference pattern(s) and of the remainder of the frequency range to be standardized, storing, in each spectrometer or one or more computers connected thereto, said standardizing parameters, the respective standardization samples having substantially identical chemical compositions so that they correspond to the same respective desired standard response, so that each of the standardized spectrometers, when presented with the same unknown sample, using the stored standardization parameters, will generate substantially identical optical spectra, wherein, in each of the plurality of spectrometers, no additional optical elements are introduced in the light path, the effect of which elements introduces an additional effect which is not present when performing measurements on normal samples.

41. A method according to claim 40, wherein, in each spectrometer, the standardization sample is introduced and handled in the spectrometer in the same manner as unknown samples to be measured are introduced.

42. A method according to claim 40, wherein each spectrometer is a spectrometer adapted to handle liquid samples, and the standardization sample is a liquid sample.

43. A method according to claim 40, wherein, in each spectrometer, the characteristic pattern(s) comprise(s) one or more local maxima or minima in the optical spectrum or in one of its derivatives.

44. A method according to claim 43, wherein, in each spectrometer, the characteristic pattern (s) comprise (s) one or more local maxima or minima in the optical spectrum positioned at fixed frequencies on the frequency axis of the spectrum.

45. A method according to claim 44, wherein, in each spectrometer, the fixed frequencies are frequencies characteristic to the identity of one or more chemical constituents of the standardization sample.

46. A method according to claim 40, wherein the components of the standardization sample(s) the identity of which is decisive to the frequencies of the local maxima or minima are selected from mixtures of water and lower alcohols.

47. A method according to claim 46, wherein the components are constituted by a mixture of water and propanol.

48. A method according to claim 40, wherein the concentrations of the components of the standardization sample(s) is/are kept within such tolerances that any error on the amplitude axis of the spectrum ascribable to concentration variations in the standardization sample is less than the repeatability of the spectrometer.

49. A method according to claim 40, wherein, in each spectrometer, the comparison of the information relating to the measured pattern(s) to corresponding information relating to the reference pattern(s) comprises identifying the frequencies in the measured pattern(s) at which local maxima or minima corresponding to local maxima or minima in the reference pattern(s) are positioned.

50. A method according to claim 40, wherein, in each spectrometer, the determination of standardizing parameters comprises determining the relation between the identified frequencies in the measured pattern(s) and the corresponding frequencies in the reference pattern(s) and obtaining parameters describing the frequency relation.

51. A method according to claim 50, wherein, in each spectrometer, the generated optical spectrum is transformed using the parameters describing the frequency relation so as to obtain a transformed spectrum in which at least the identified local maxima or minima are positioned at substantially the same frequencies as in the reference pattern(s).

52. A method according to claim 51, further comprising, in each spectrometer, comparing, over at least one frequency range, the amplitude of the frequency-transformed spectrum and the corresponding amplitude of the reference pattern(s) and obtaining standardization parameters describing the relation between the amplitude of the frequency-transformed spectrum and the amplitude of the reference pattern(s).

53. A method according to claim 40, wherein, in each spectrometer, the determination of standardizing parameters comprises determining the relation between the amplitudes of the measured pattern(s) at the identified frequencies and the amplitudes of the reference pattern(s) at the corresponding frequencies and obtaining parameters describing the relation.

54. A method according to claim 40, wherein, in each spectrometer, the reference pattern(s) is/are derived from a spectrum or spectra generated by a spectrometer on the basis of at least one sample of substantially the same chemical composition(s) as the at least one standardization sample(s).

55. A method according to claim 40, wherein characteristic pattern(s) of the optical spectrum of the at least one standardization sample is/are known or optionally predefined at the time of generating the optical spectrum from the at least one standardization sample.

56. A method according to claim 40, wherein the at least one standardization sample is of a type which is different in chemical composition from the unknown sample.

57. A method according to claim 40, wherein, in each spectrometer, the model assumes an interrelation between the positions on the frequency axis of at least parts of the characteristic patterns of the optical spectrum of the at least one standardization sample and the corresponding parts of the reference patterns.

58. A method according to claim 40, wherein, in each spectrometer, the model assumes an interrelation between the positions on the absorption axis of at least parts of the characteristic patterns of the optical spectrum of the at least one standardization sample and the corresponding parts of the reference patterns.

59. A method according to claim 40, wherein, in each spectrometer, 1–100, such as 1–80, preferably 1–10, such as 2–5, preferably 2 characteristic patterns and/or reference patterns are used.

60. A method according to claim 40, wherein, in each spectrometer, the one or more predetermined frequency ranges cover not more than 90%, such as not more than 70%, preferably not more than 50%, such as not more than 30%, preferably not more than 20%, such as not more than 10%, preferably not more than 5% of the frequency range to be standardized.

* * * * *